(12) United States Patent
Kim et al.

(10) Patent No.: US 12,005,271 B2
(45) Date of Patent: Jun. 11, 2024

(54) SUPER RESOLUTION MAGNETIC RESONANCE (MR) IMAGES IN MR GUIDED RADIOTHERAPY

(71) Applicant: Washington University, St. Louis, MO (US)

(72) Inventors: Taeho Kim, St. Louis, MO (US); Geoffrey Hugo, St. Louis, MO (US); Zhen Ji, St. Louis, MO (US); Matthew Schmidt, St. Louis, MO (US); Yu Wu, St. Louis, MO (US)

(73) Assignee: Washington University, St. Louis, MO (US)

( * ) Notice: Subject to any disclaimer, the term of this patent is extended or adjusted under 35 U.S.C. 154(b) by 220 days.

(21) Appl. No.: 17/661,768

(22) Filed: May 3, 2022

(65) Prior Publication Data

US 2022/0362584 A1 Nov. 17, 2022

Related U.S. Application Data

(60) Provisional application No. 63/183,282, filed on May 3, 2021.

(51) Int. Cl.
*A61N 5/00* (2006.01)
*A61B 5/055* (2006.01)
*A61N 5/10* (2006.01)

(52) U.S. Cl.
CPC ............ *A61N 5/1069* (2013.01); *A61B 5/055* (2013.01); *A61N 2005/1055* (2013.01); *A61N 2005/1056* (2013.01)

(58) Field of Classification Search
CPC .......... A61N 5/1069; A61N 2005/1055; A61N 2005/1056; A61B 5/055
See application file for complete search history.

(56) References Cited

U.S. PATENT DOCUMENTS

| | | | | |
|---|---|---|---|---|
| 2015/0297916 | A1* | 10/2015 | Chen | G06T 7/13 600/1 |
| 2016/0100773 | A1* | 4/2016 | Ching | A61B 34/20 600/424 |
| 2016/0143576 | A1* | 5/2016 | Symon | A61N 5/1049 600/411 |
| 2018/0314906 | A1* | 11/2018 | Yang | G06V 10/462 |
| 2020/0238102 | A1* | 7/2020 | Lamb | G16H 20/40 |
| 2023/0302297 | A1* | 9/2023 | Lachaine | A61N 5/1039 |

OTHER PUBLICATIONS

Tran et al., "Evaluation of MRI-derived surrogate signals to model respiratory motion" Biomed Phys Eng Express. Jul. 2020; 6(4): 045015 (Published online Jun. 12, 2020) (Year: 2020).*

(Continued)

*Primary Examiner* — Colin T. Sakamoto
(74) *Attorney, Agent, or Firm* — Armstrong Teasdale LLP

(57) ABSTRACT

A computer implemented method of treatment targeting includes receiving magnetic resonance (MR) images of a subject including a target region, generating at least one contour of at least one surrogate element apart from the target region in the MR images, and determining a location of the target region in each of the MR images based on a location of the at least one contour in the MR images.

20 Claims, 25 Drawing Sheets
(19 of 25 Drawing Sheet(s) Filed in Color)

(56) References Cited

OTHER PUBLICATIONS

Dawson et al., "Imaging in radiation oncology: a perspective," Oncologist, 15(4): 338-349 (2010). doi:10.1634/theoncologist.2009-S106.
Saw et al., "Immobilization devices for intensity-modulated radiation therapy (IMRT)," Medical Dosimetry, 26(1): 71-77 (2001). doi:https://doi.org/10.1016/S0958-3947(00)00059-5.
Stemkens et al., "Effect of intra-fraction motion on the accumulated dose for free-breathing MR-guided stereotactic body radiation therapy of renal-cell carcinoma," Phys Med Biol, 62(18): 7407-7424 (2017). doi: 10.1088/1361-6560/aa83f7.
Waghorn et al., "Analyzing the impact of intrafraction motion: Correlation of different dose metrics with changes in target D95%," Medical Physics, 38(8): 4505-4511 (2011). doi:https://doi.org/10.1118/1.3605633.
Suh et al., "An analysis of thoracic and abdominal tumour motion for stereotactic body radiotherapy patients," Phys Med Biol, 53(13): 3623-3640 (2008). doi:10.1088/0031-9155/53/13/016.
Bussels et al., "Respiration-induced movement of the upper abdominal organs: a pitfall for the three-dimensional conformal radiation treatment of pancreatic cancer," Radiother Oncol, 68(1): 69-74 (2003). doi:10.1016/s0167-8140(03)00133-6.
Feng et al., "Characterization of pancreatic tumor motion using cine MRI: surrogates for tumor position should be used with caution," Int J Radiat Oncol Biol Phys, 74(3): 884-891 (2009). doi:10.1016/j.ijrobp.2009.02.003.
Eccles et al., "Reproducibility of liver position using active breathing coordinator for liver cancer radiotherapy," Int J Radiat Oncol Biol Phys, 64(3): 751-759 (2006). doi:10.1016/j.ijrobp.2005.05.066.
Zeng et al., "Intrafraction tumor motion during deep inspiration breath hold pancreatic cancer treatment," J Appl Clin Med Phys, 20(5): 37-43 (2019). doi: 10.1002/acm2.12577.
Wunderink et al., "Potentials and limitations of guiding liver stereotactic body radiation therapy set-up on liver-implanted fiducial markers," Int J Radiat Oncol Biol Phys, 77(5): 1573-1583 (2010). doi:10.1016/j.ijrobp.2009.10.040.
Murphy et al., "Full-dose gemcitabine and concurrent radiotherapy for unresectable pancreatic cancer," Int J Radiat Oncol Biol Phys, 68(3): 801-808 (2007). doi: 10.1016/j.ijrobp.2006.12.053.
Gurka et al., "Stereotactic body radiation therapy with concurrent full-dose gemcitabine for locally advanced pancreatic cancer: a pilot trial demonstrating safety," Radiat Oncol, 8(1): 1-9 (2013). doi:10.1186/1748-717X-8-44.
Van Der Geld et al., "Evaluation of four-dimensional computed tomography-based intensity-modulated and respiratory-gated radiotherapy techniques for pancreatic carcinoma," Int J Radiat Oncol Biol Phys, 72(4): 1215-1220 (2008). doi: 10.1016/j.ijrobp.2008.07.010.
Henke et al., "Adaptive MR-Guided Stereotactic Body Radiation Therapy (AMR-SBRT) for Oligometastatic or Unresectable Primary Abdominal Malignancies: Results of a Prospective Phase I Trial," International Journal of Radiation Oncology Biology Physics, 96(2): E205-E206 (2016). doi:https://doi.org/10.1016/j.ijrobp.2016.06.1108.
Henke et al., "Phase I trial of stereotactic MR-guided online adaptive radiation therapy (SMART) for the treatment of oligometastatic or unresectable primary malignancies of the abdomen," Radiother Oncol, 126(3): 519-526 (2018). doi:10.1016/j.radonc.2017.11.032.
Rudra et al., "Using adaptive magnetic resonance image-guided radiation therapy for treatment of inoperable pancreatic cancer," Cancer Med, 8(5): 2123-2132 (2019). doi:10.1002/cam4.2100.
Chan, et al., "Active contours without edges. IEEE Trans Image Process," 10(2): 266-277 (2001). doi:10.1109/83.902291.
Knybel et al., "The analysis of respiration-induced pancreatic tumor motion based on reference measurement," Radiation Oncology, 9(1): 1-8 (2014). doi: 10.1186/1748-717X-9-192.
Dolde et al., "4DMRI-based investigation on the interplay effect for pencil beam scanning proton therapy of pancreatic cancer patients," Radiation Oncology, 14(1): 1-13 (2019). doi:10.1186/s13014-019-1231-2.
Keall et al., "The management of respiratory motion in radiation oncology report of AAPM Task Group 76," Med Phys, 33(10): 3874-3900 (2006). doi:10.1118/1.2349696.
Brandner et al., "Motion management strategies and technical issues associated with stereotactic body radiotherapy of thoracic and upper abdominal tumors: A review from NRG oncology," Medical Physics, 44(6): 2595-2612 (2017). doi:10.1002/mp.12227.
Lewis et al., "A pressure based respiratory motion management system with biofeedback for MR-based radiotherapy," Biomedical Physics Engineering Express, 5(3): 037003 (2019). 5doi:10.1088/2057-1976/ab0157.
Chun et al., "Evaluation of super-resolution on 50 pancreatic cancer patients with real-time cine MRI from 0.35T MRgRT," Biomed Phys Eng Express, 7(5): 055020 (2021). doi: 10.1088/2057-1976/ac1c51. PMID: 34375963.
Chun et al., "MRI super-resolution reconstruction for MRI-guided adaptive radiotherapy using cascaded deep earning: In the presence of limited training data and unknown translation model," Med Phys, 46(9): 4148-4164 (2019).

* cited by examiner

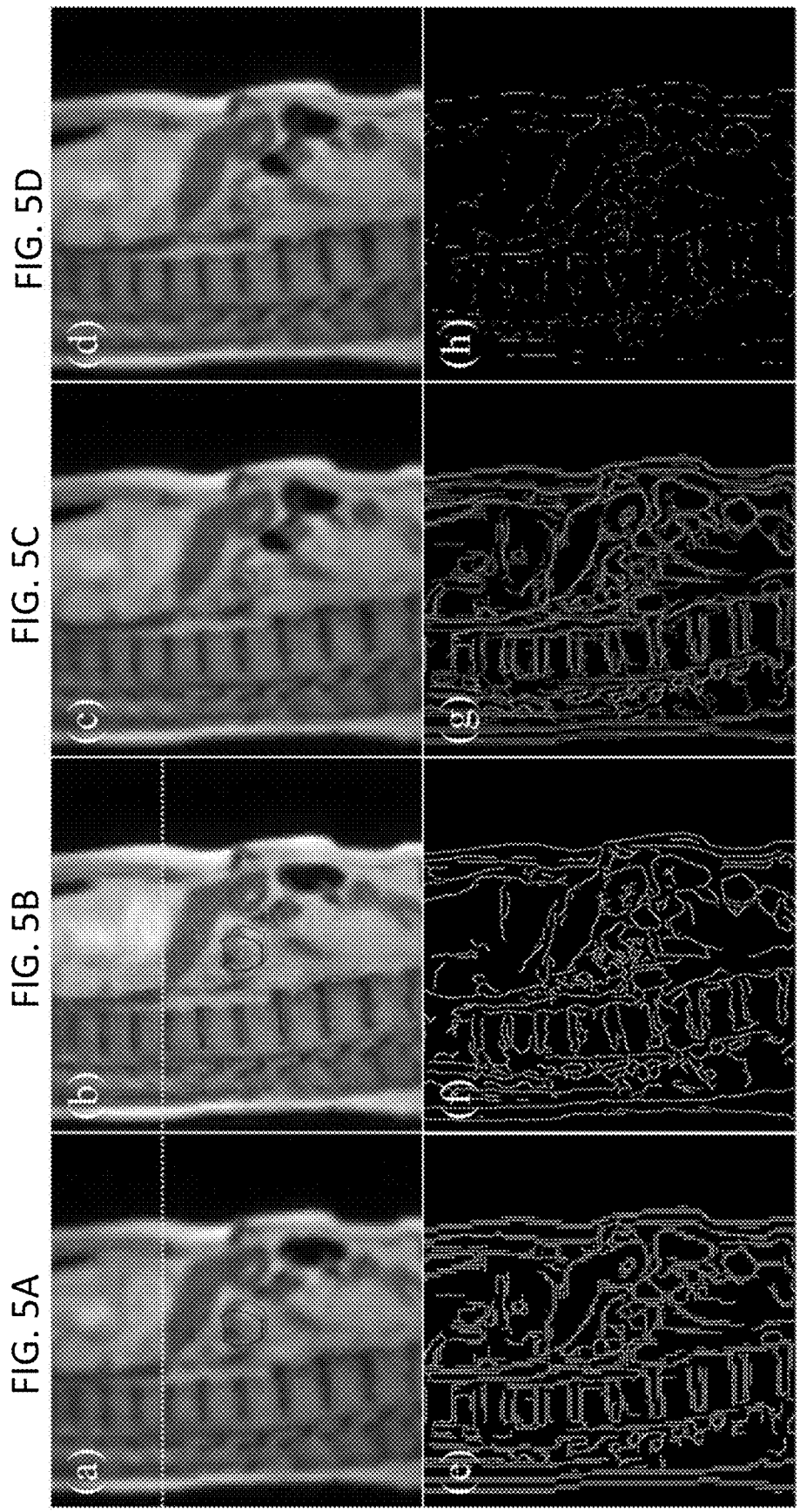

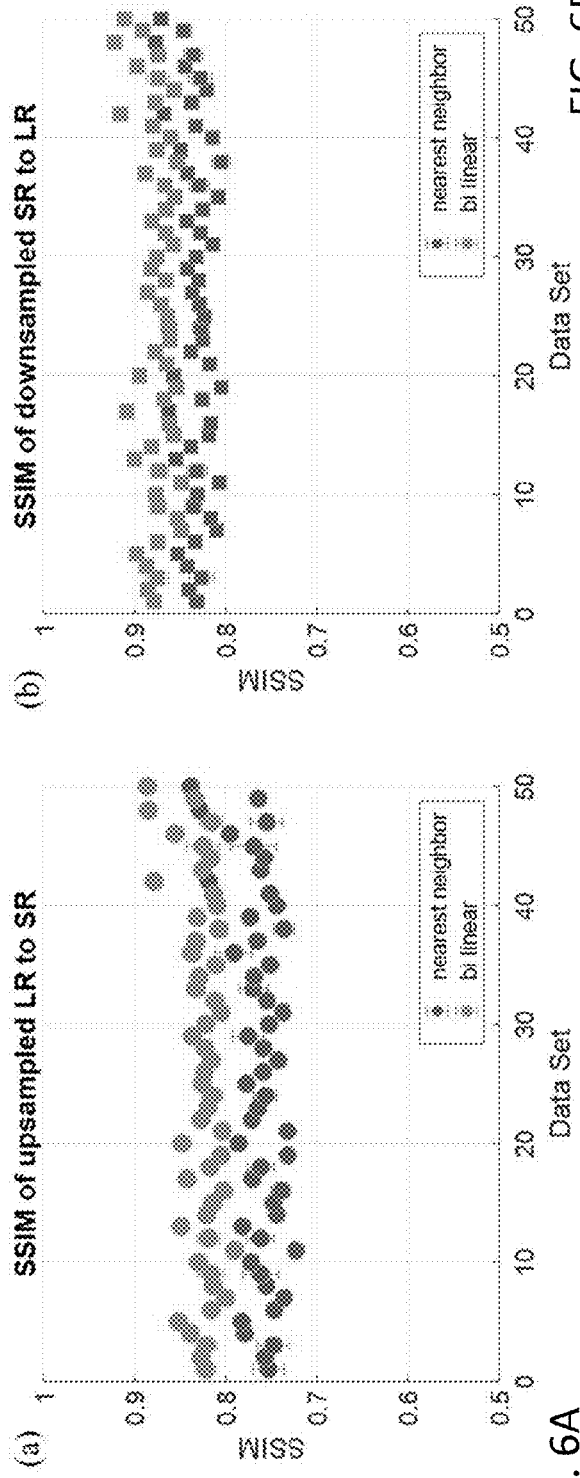
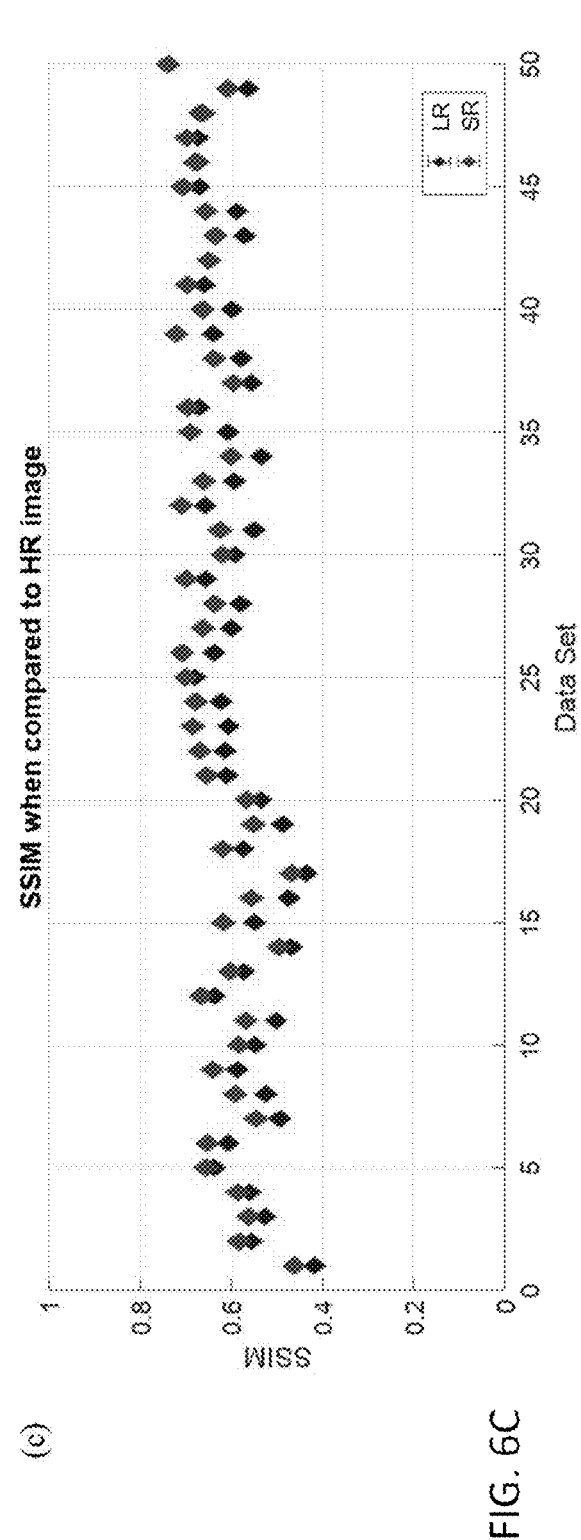
FIG. 6A
FIG. 6B
FIG. 6C

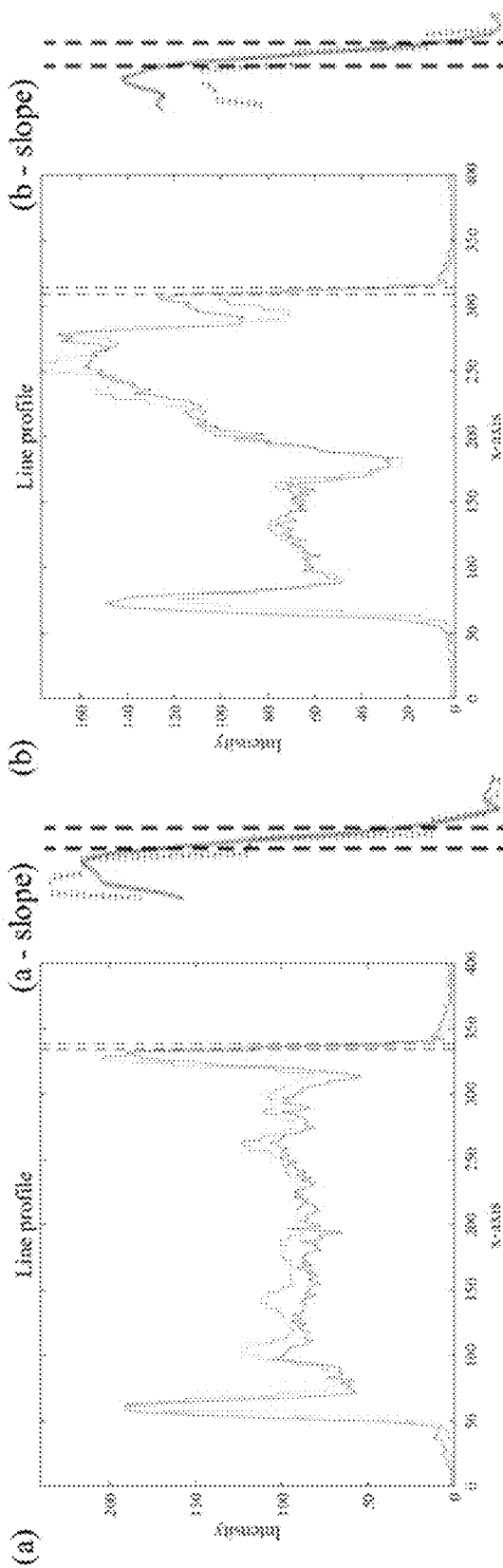
FIG. 7A
FIG. 7B
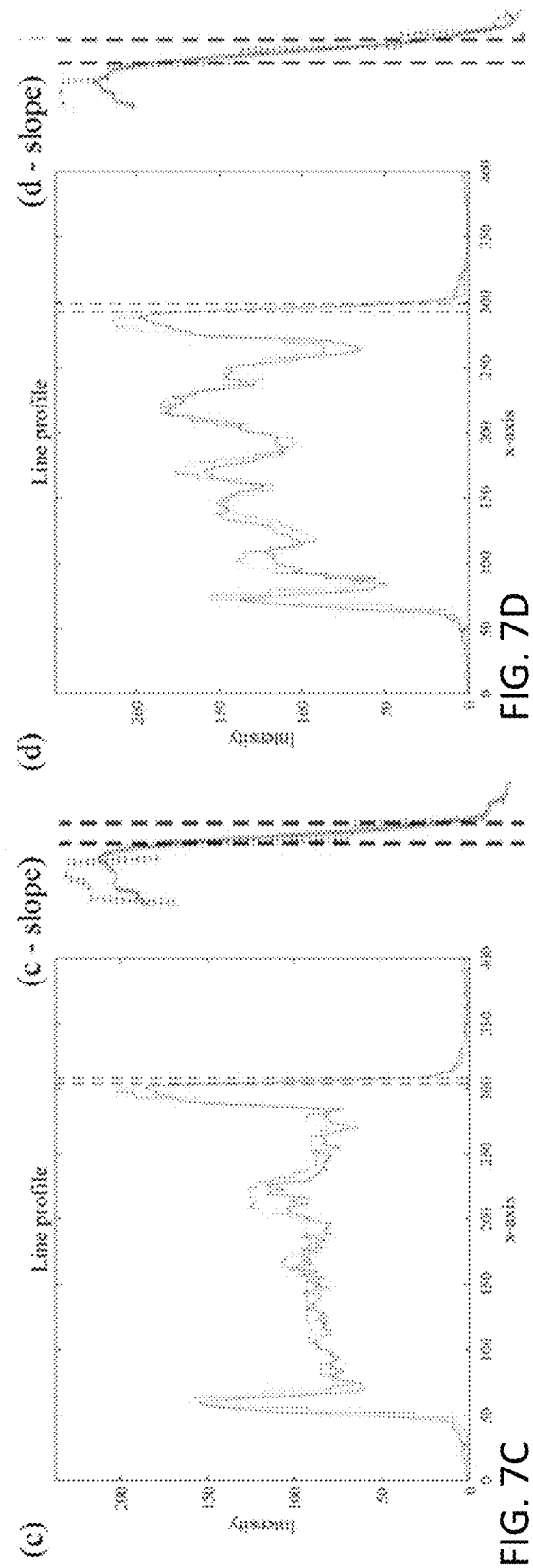
FIG. 7C
FIG. 7D

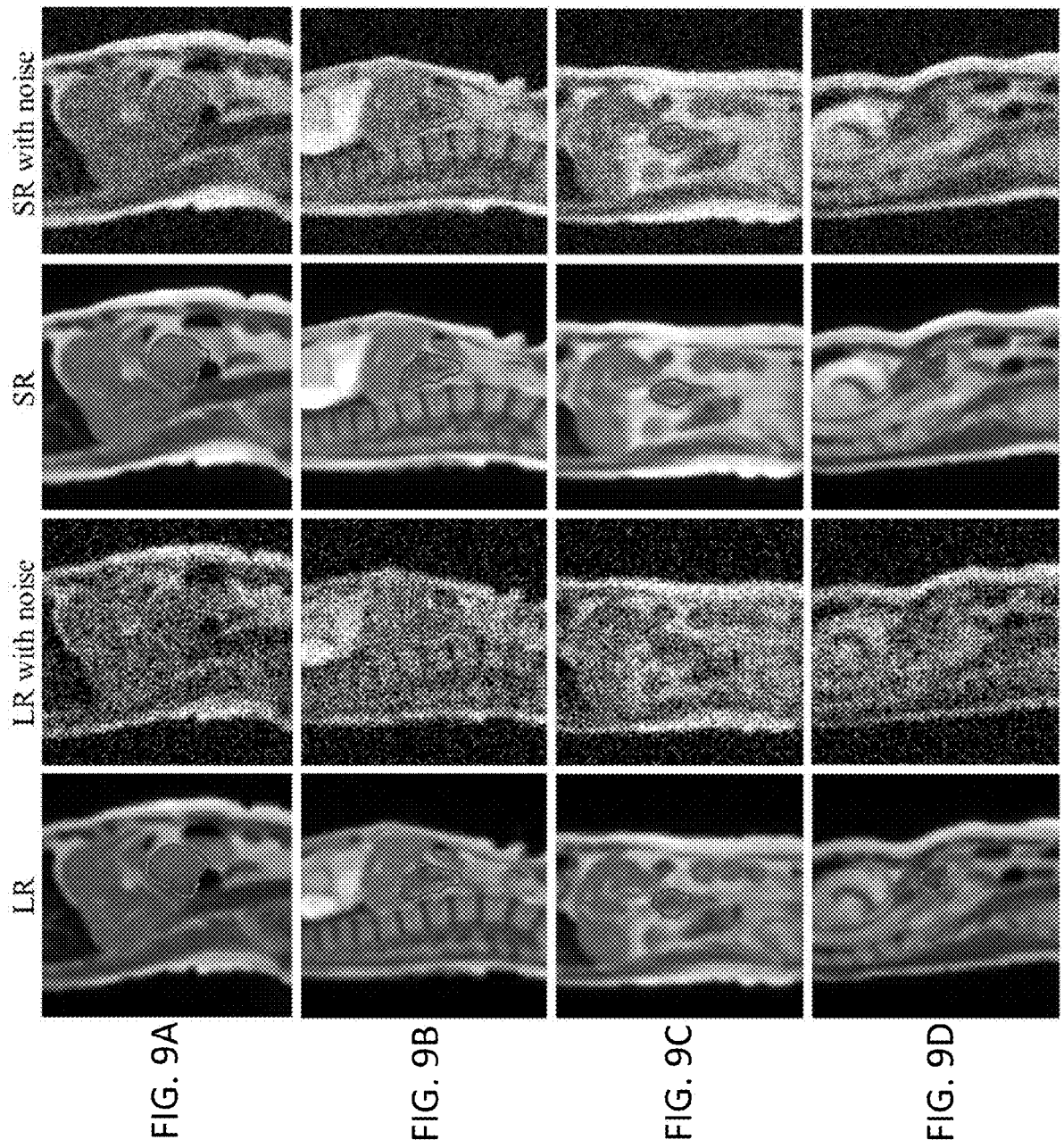

SUPER RESOLUTION MAGNETIC RESONANCE (MR) IMAGES IN MR GUIDED RADIOTHERAPY

CROSS REFERENCE TO RELATED APPLICATION

This application claims priority to U.S. provisional application No. 63/183,282 filed May 3, 2021, which is incorporated herein in its entirety.

BACKGROUND

The field of the disclosure relates generally to radiotherapy, and more particularly, to systems and methods of increasing imaging resolution of magnetic resonance (MR) images used to guide radiotherapy.

MR guided radiotherapy (MRgRT) with an integrated MR imaging (MRI) and radiotherapy delivery system provides onboard imaging with excellent soft-tissue contrast without additional radiation exposure, enabling real-time tumor tracking, and the capability to perform online adaptive radiation therapy (ART). Known adaptive radio therapy systems and methods are disadvantaged in some aspects and improvements are desired.

This background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

One aspect of this disclosure is a treatment targeting system including a computing device having a processor and a memory. The memory stores instructions that when executed by the processor cause the processor to receive magnetic resonance (MR) images of a subject including a target region, generate at least one contour of at least one surrogate element apart from the target region in the MR images, and determine a location of the target region in each of the MR images based on a location of the at least one contour in the MR images.

Another aspect of this disclosure is a computer implemented method of treatment targeting. The method includes receiving magnetic resonance (MR) images of a subject including a target region, generating at least one contour of at least one surrogate element apart from the target region in the MR images, and determining a location of the target region in each of the MR images based on a location of the at least one contour in the MR images.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate several embodiments and together with the description illustrate the disclosed compositions and methods.

FIGS. 5A-H depict example images with structural similarity and varied resolution.

FIGS. 6A-6C depict SSIM values for upsampled and downsampled resolution.

FIGS. 7A-7D depict line profiles of LR and SR images for four different patients.

FIGS. 8A-8D depicts shape similarity and DICE coefficients and the change in the metrics with the addition of noise.

FIGS. 9A-9D depicts images for four different patients with different BRISQUE ratings.

Figure 10:
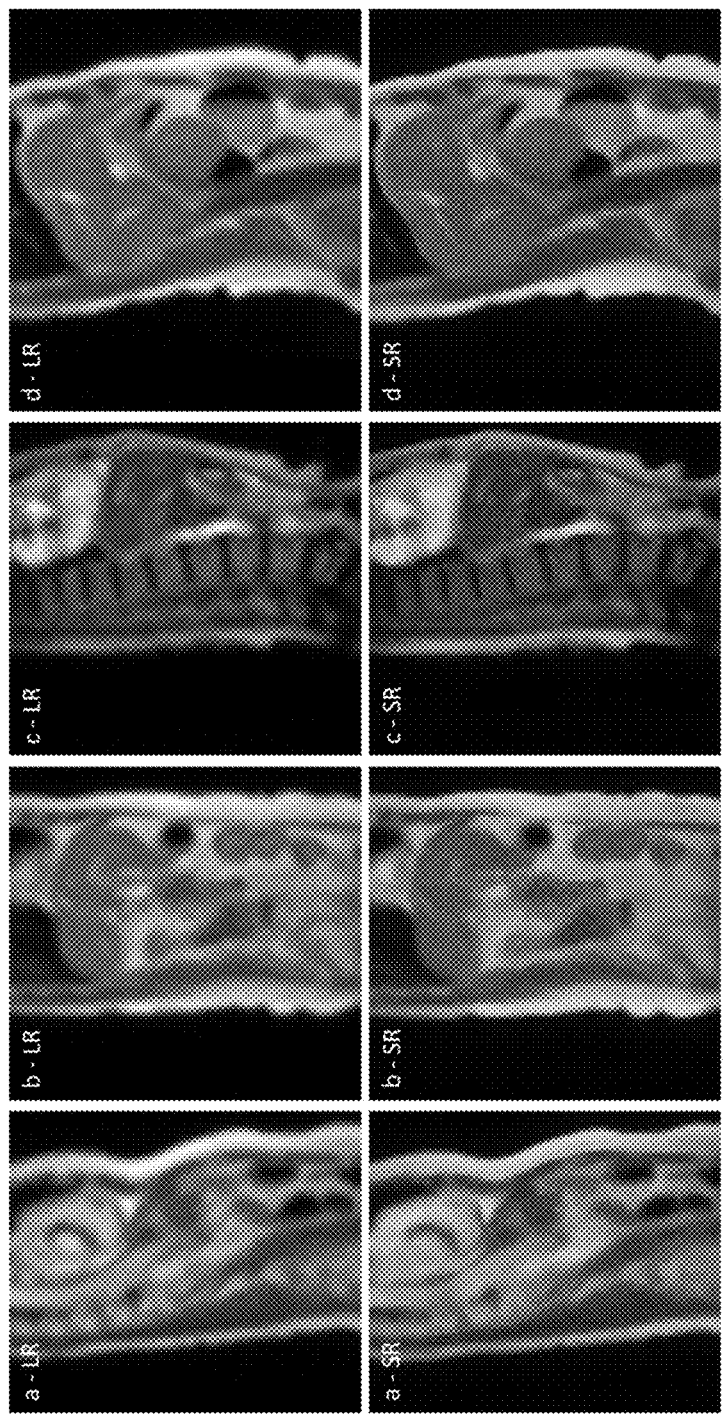

FIG. 10 depicts low resolution and super resolution images for four different patients.

Figure 11:
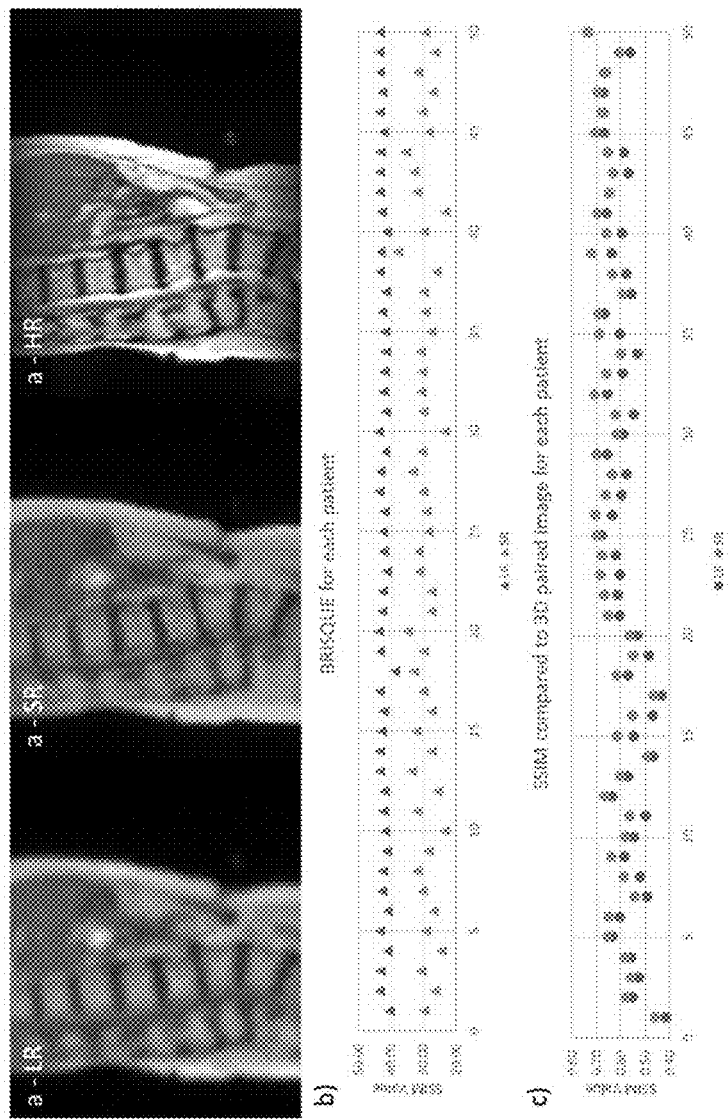

FIG. 11 depicts low, super and 3D high resolution images from one patient, BRISQUE values for all patients, and SSIM values for all patients compared to paired high resolution 3D images.

Figure 12:
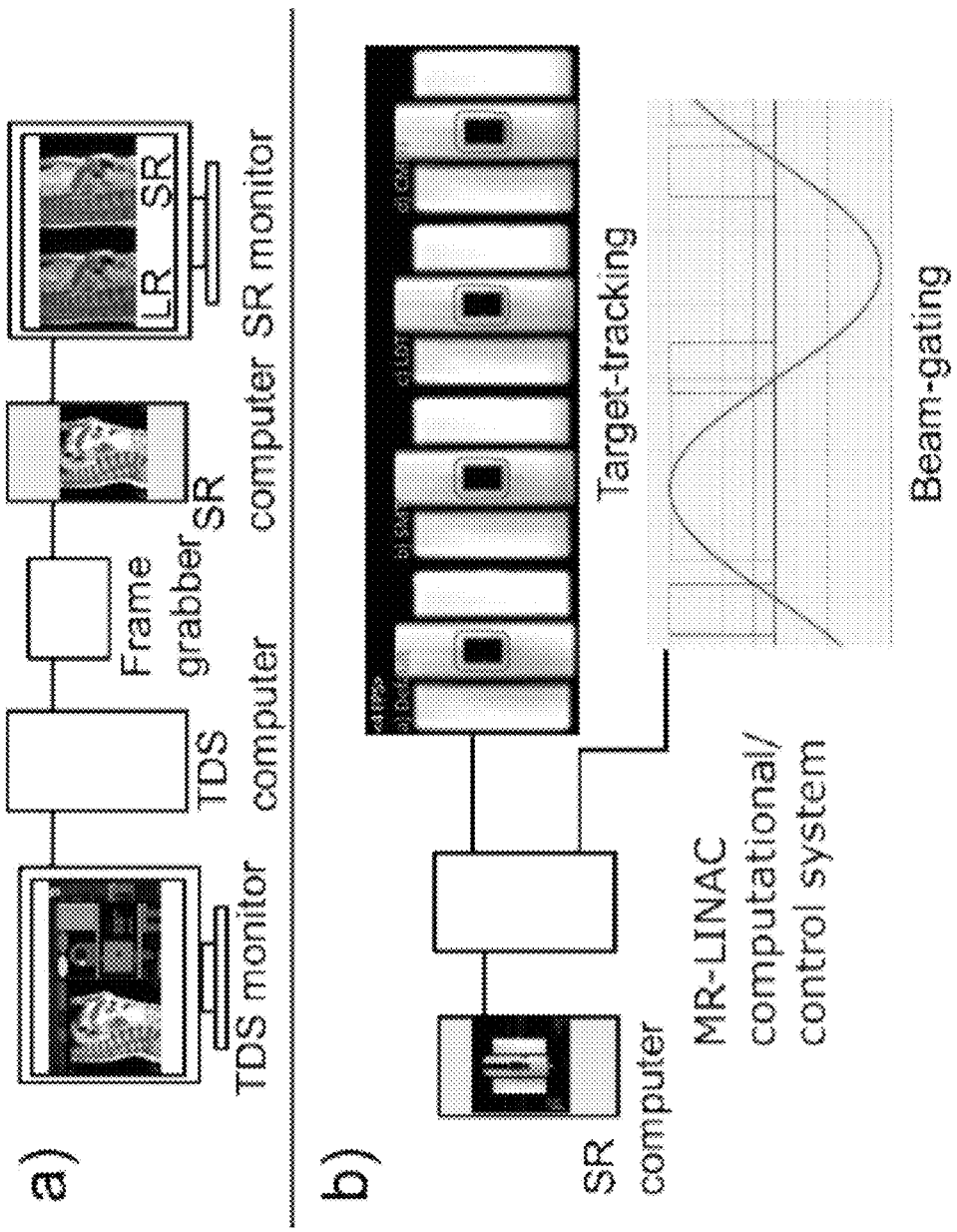

FIG. 12 depicts a schematic of one embodiment.

Figure 13:
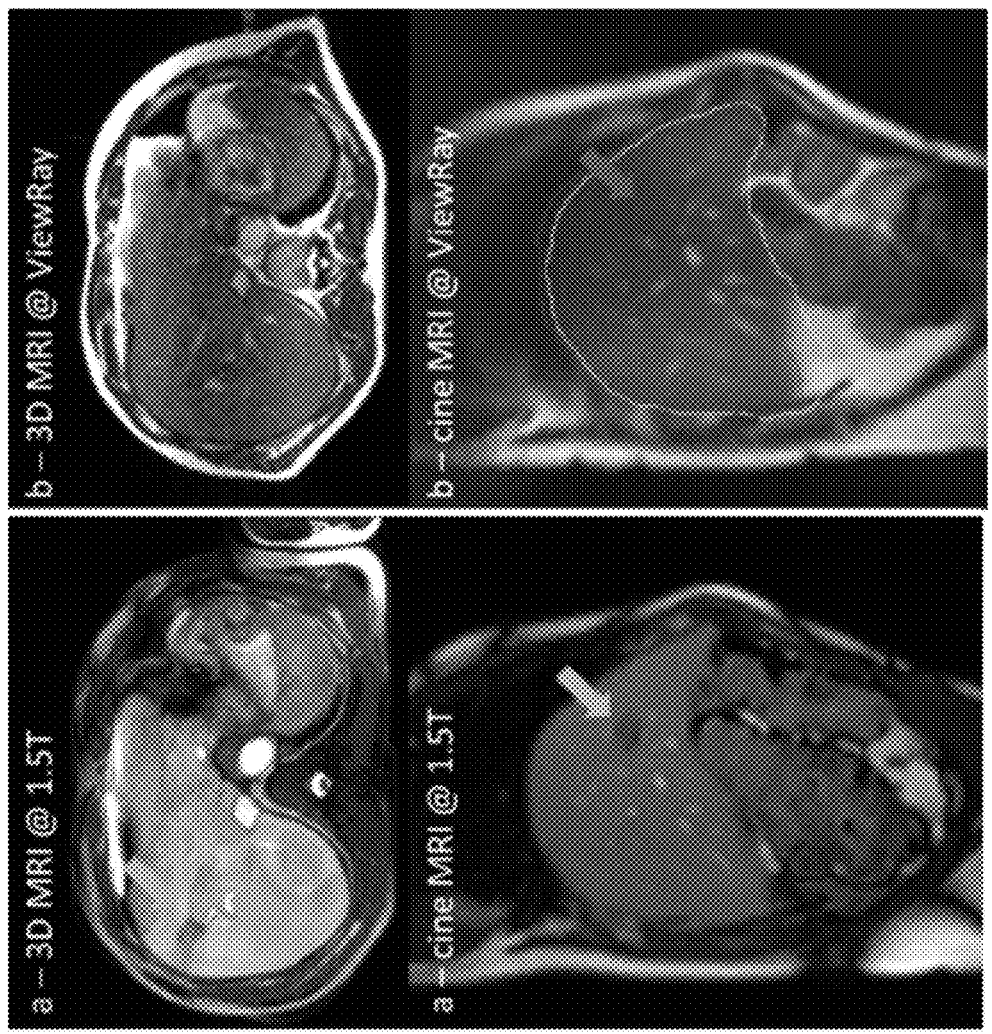

FIG. 13 depicts liver MRIs.

Figure 14:

FIG. 14 depicts super resolution MRI images and an example system used to obtain the images.

Figures 15A, 15B, 15C:
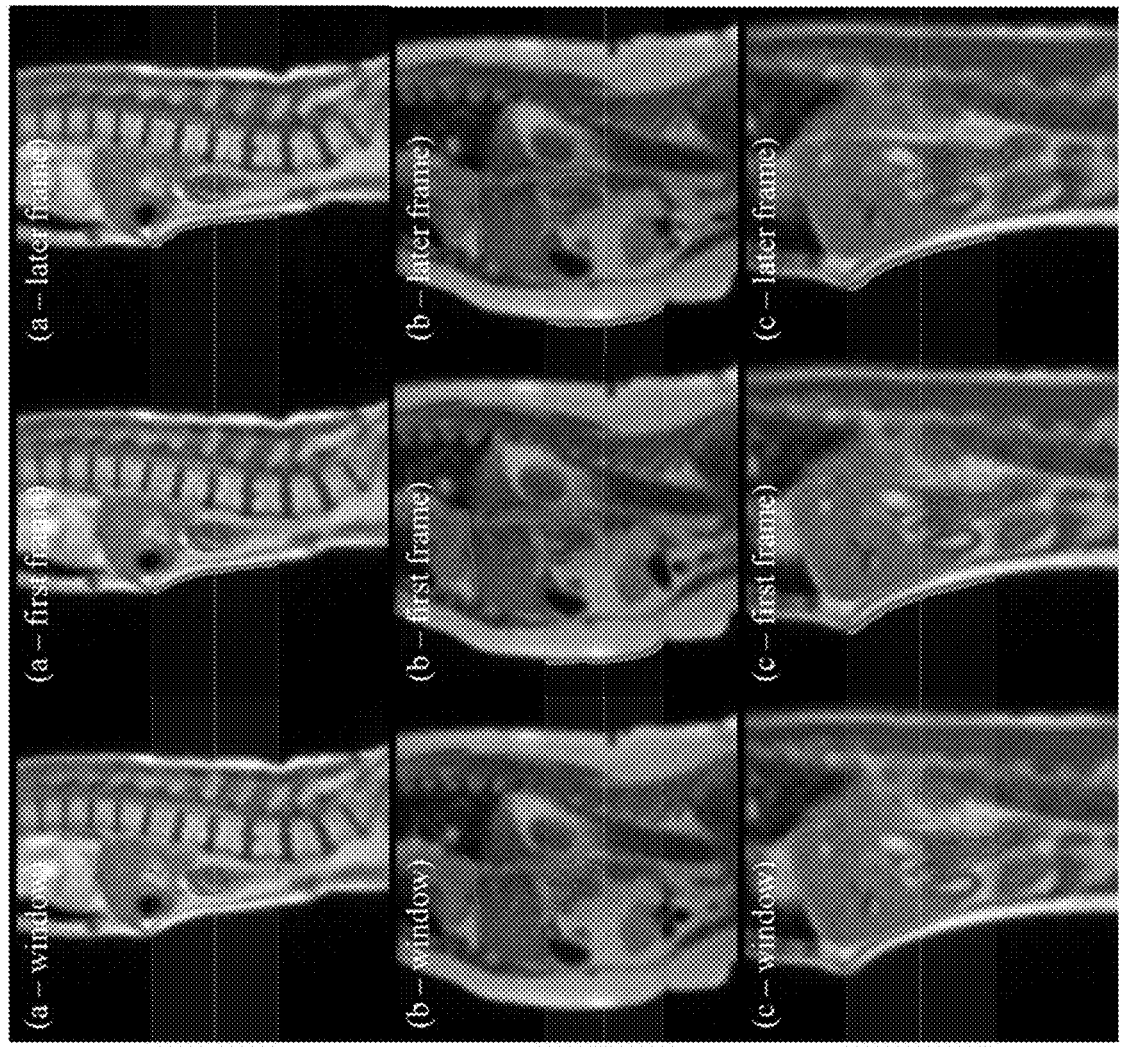

FIGS. 15A-15C depicts images from the MAXgRT software.

Figure 16:
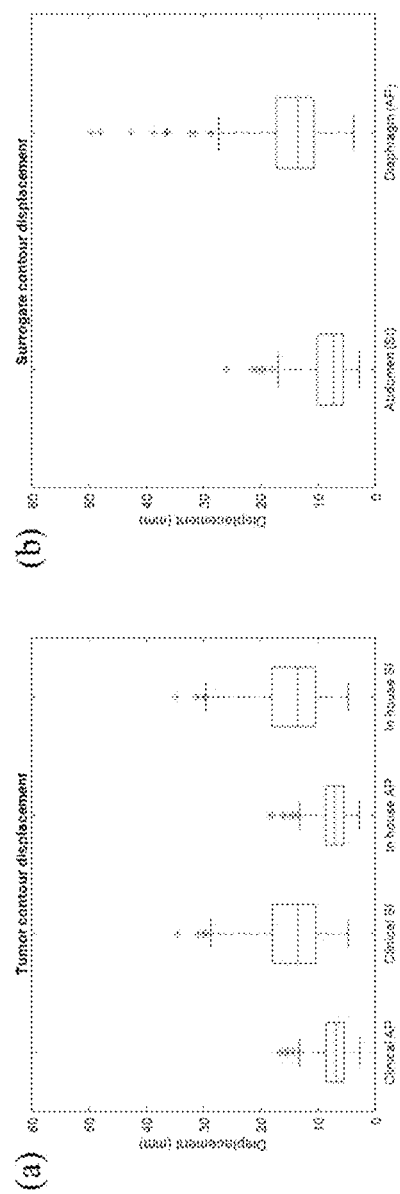

FIG. 16 depicts tumor contour displacement for clinical and in-house tumor contours.

Figure 17:
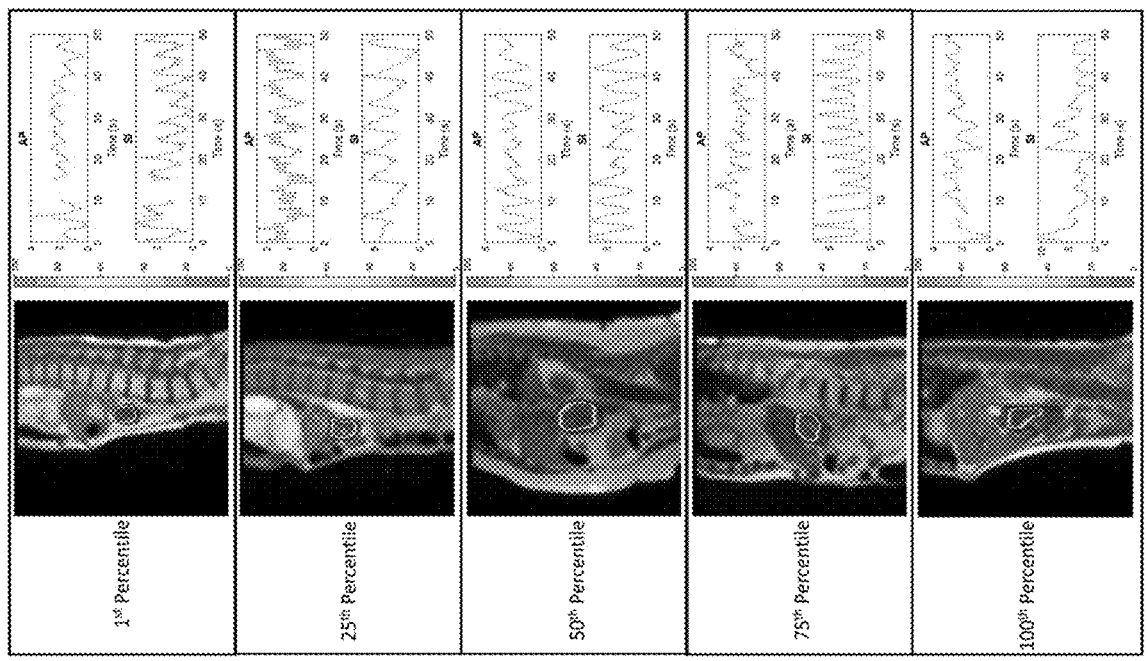

FIG. 17 depicts intra-fraction variation of pancreatic tumor contour position normalized to the number of total acquired frames for five patients.

Figure 18:
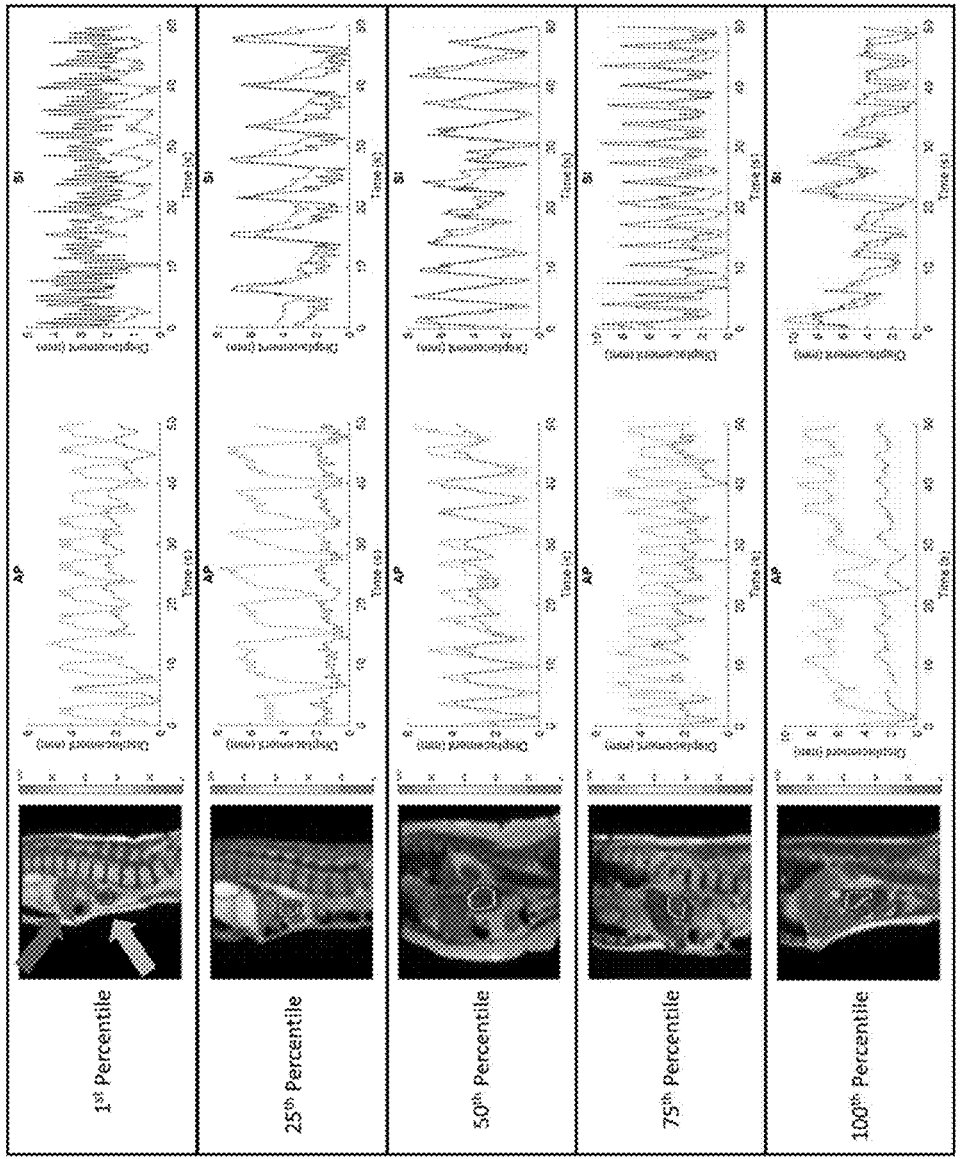

FIG. 18 depicts pancreatic tumor and surrogate contour motion in the anterior-posterior and superior-inferior directions for five patients.

Figure 19:
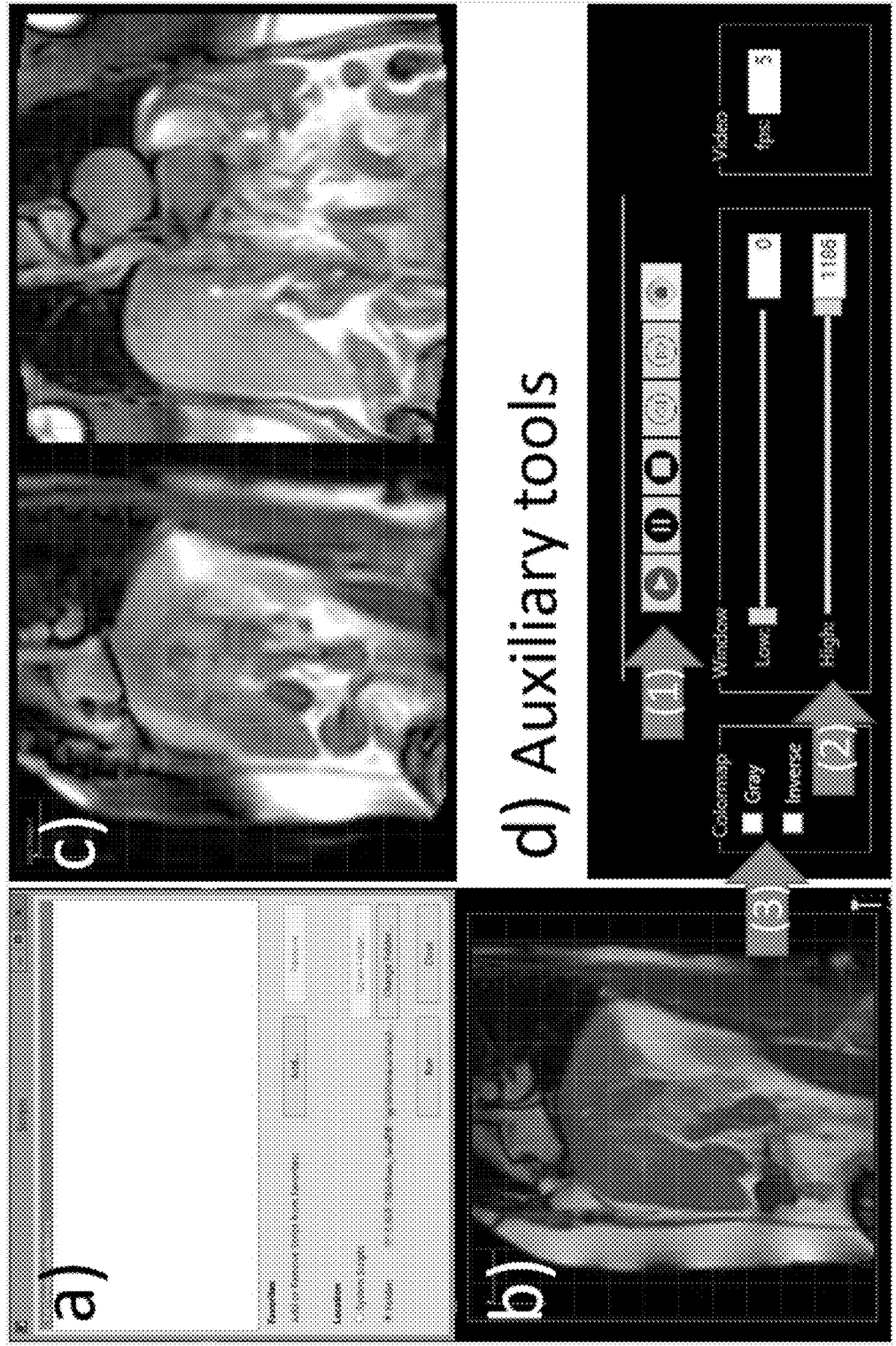

FIG. 19 depicts a programming interface and display panel.

Figure 20:
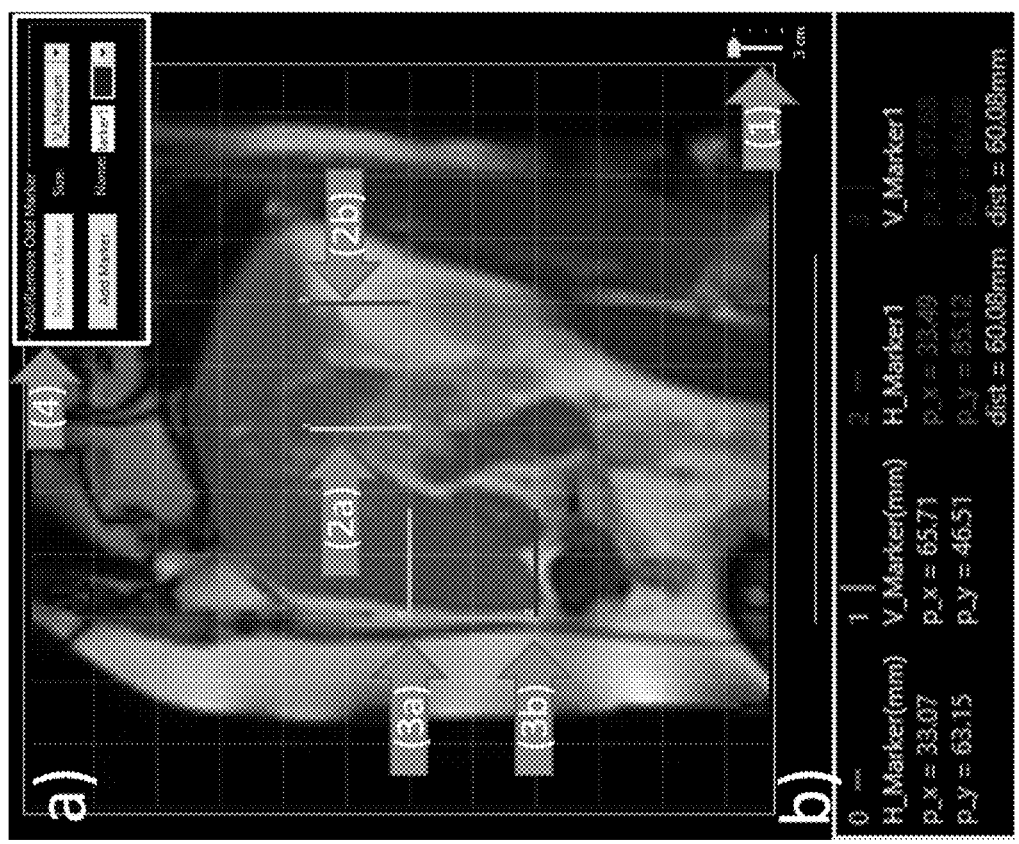

FIG. 20 depicts tumor motion range and measurement tools.

Figure 21:
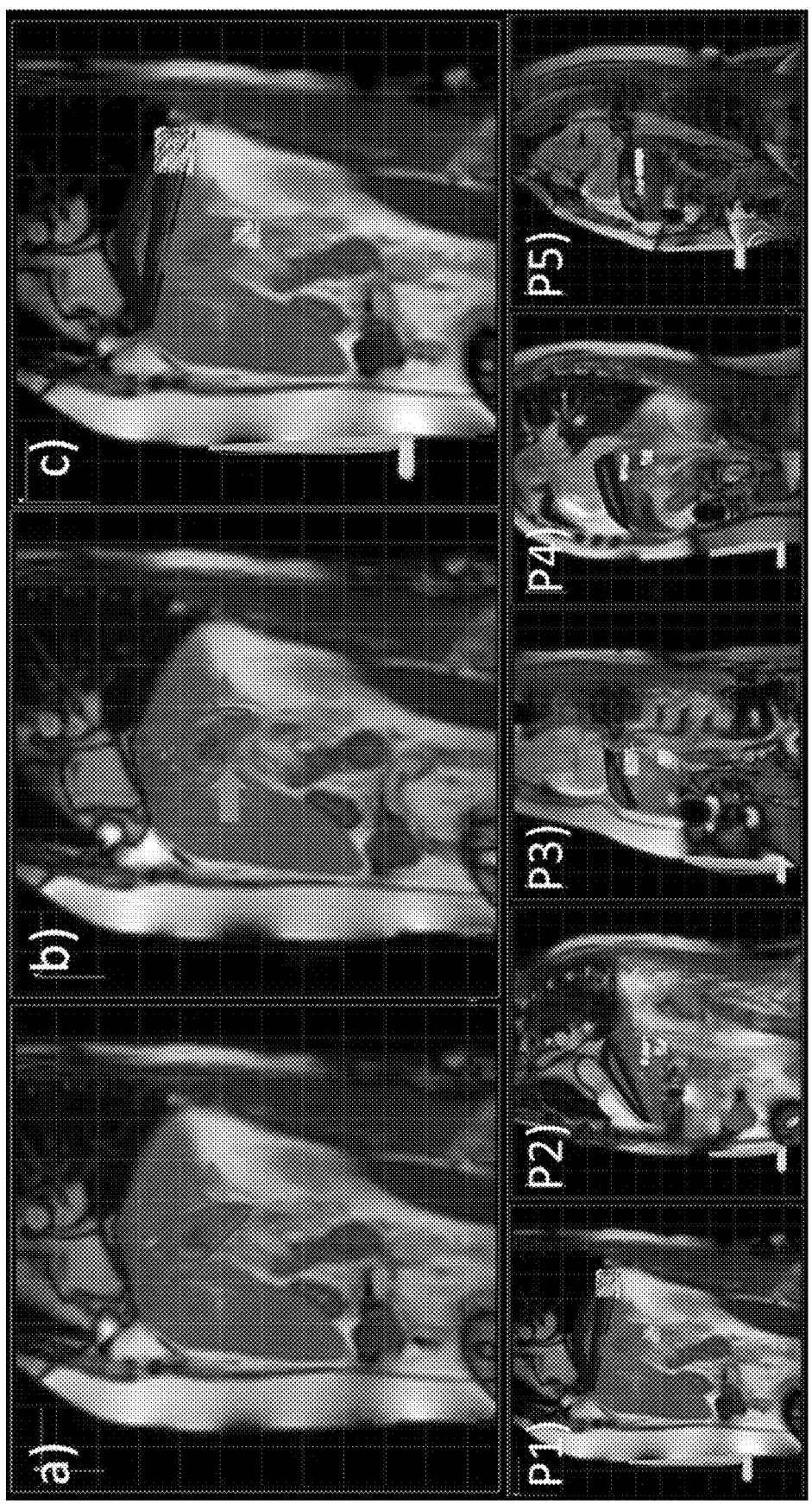

FIG. 21 depicts a manual contouring tool.

Figure 22:
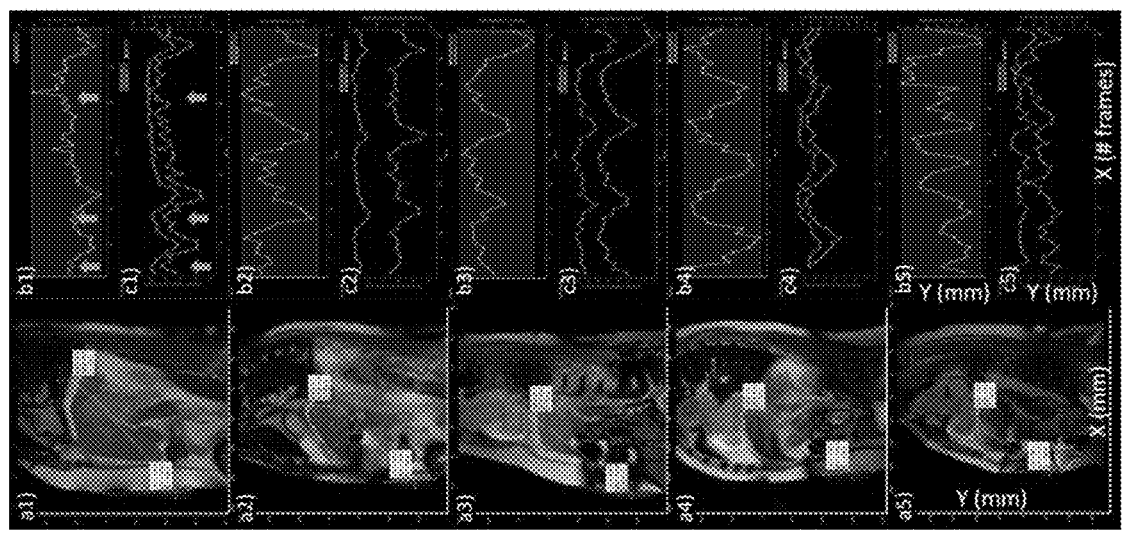

FIG. 22 depicts an examination of motion correlation between the tumor and the surrogate motion.

Figure 23:
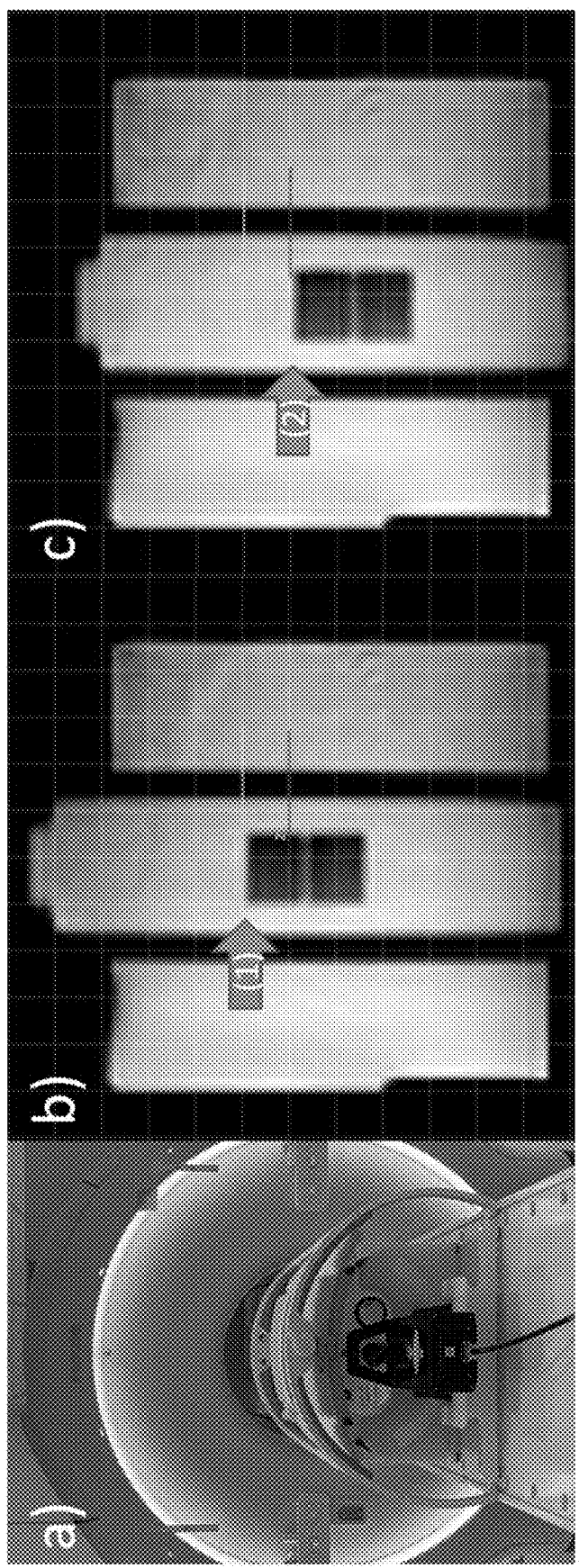

FIG. 23 depicts a measurement of a motion phantom.

DETAILED DESCRIPTION

The disclosure includes systems and methods of increasing image resolution of the magnetic resonance (MR) images of a subject using a neural network model. As used herein, a subject is a human, an animal, or a phantom.

MR guided radiotherapy (MRgRT) provides onboard imaging with excellent soft-tissue contrast without additional radiation exposure from the magnetic resonance imaging (MRI) system, enabling real-time tumor tracking, and the capability to perform online adaptive radiation therapy (ART).

Current onboard MRI systems, however, face the problem of limited spatial resolution related inversely to scanning time, especially on low-field MRI systems (<1.5 T). To obtain high-resolution MR images multiple changes may be made to acquisition parameters including increased acquisition time, narrowing the field of view, and reducing the signal-to-noise ratio (SNR). However, increasing image acquisition time may increase the presence of motion blurring, narrowed field of view limits the dose calculation volume, and reduced SNR may prevent anatomical structure identification. In MRgRT, the resolution of the MRI fundamentally determines setup uncertainty, the accuracy of target definition, and tracking precision. Therefore, scan time should be minimized while maximizing the spatial resolution of the MRI. This is especially true for target tracking with cine MRI, which requires the acquisition of multiple images every second to provide adequate tracking accuracy due to the period, amplitude, and irregularity of respiratory motion.

For example, currently, the ViewRay MR-linac provides 4 frames per second (fps) 2D cine acquisitions in the sagittal plane with 3.5 mm pixel edge, and 8 fps acquisition with a 2.4 mm pixel edge utilizing a data sharing method, and a slice thickness of 5, 7, or 10 mm. The 8 fps method provides higher spatiotemporal resolution, but the data sharing method introduces image blurring. These images sacrifice a significant level of spatial resolution, edge sharpness, and signal to noise ratio (SNR) to achieve sufficient temporal resolution, which impacts the performance of automatic tracking algorithms and target boundary identification.

The spatial resolution of MRI may be greatly improved without changing hardware or scanning parameters by utilizing imaging postprocessing techniques known as super-resolution (SR). The purpose of the SR reconstruction is to restore high-resolution (HR) image information only using low-resolution (LR) images. A robust SR volumetric MRI reconstruction framework is provided using a novel cascaded DL approach. This is the first application of the SR MRI reconstruction framework for clinical 2D cine MRI in RT.

Figure 1A:
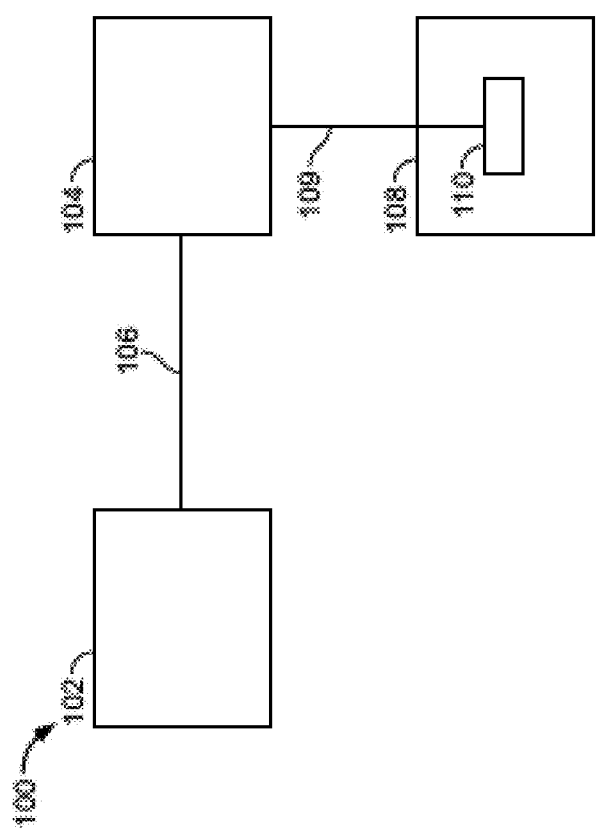
FIG. 1A is a block diagram of an exemplary system.

FIG. 1A illustrates an exemplary imaging system 100. As seen in FIG. 1A, system 100 includes a sensing system 102 for imaging a subject (not shown). In one suitable embodiment, sensing system 102 is a magnetic resonance imaging device (MRI). It should be noted that the present disclosure is not limited to any one particular type of imaging and electrical technique or device, and one of ordinary skill in the art will appreciate that the current disclosure may be used in connection with any type of technique or device that enables system 100 to function as described herein. In some embodiments, the system 100 is an MR guided radiotherapy (MRgRT) system and also includes a radiotherapy delivery system.

In the exemplary embodiment, system 100 also includes a computing device 104 coupled to sensing system 102 via a data conduit 106. The reference number 104 may be representative of multiple different computing systems located at different locations, for example (i) one computing system may be involved in controlling operation of the image acquisition process and as such may be co-locating with the MRI scanning equipment, (ii) another computing system involved in communicating and storing acquired MRI image data in an image repository (database) where the image data may be retrieved for further processing (e.g., the functional mapping function), and (iii) another computing system used in performing operations on the MRI image data described herein that may be stored in the same or a different image repository, such that the output may then be accessed for use in making medical interpretations and diagnoses including use in connection with pre-operative planning and in the operating room which may involve loading the output mapping on a separate surgical navigation system. One or more of the computing systems making up the computing device 104 may, in one embodiment, comprise a picture archiving and communication system (PACS).

It should be noted that, as used herein, the term "couple" is not limited to a direct mechanical, electrical, and/or communication connection between components, but may also include an indirect mechanical, electrical, and/or communication connection between multiple components. Sensing system 102 may communicate with computing device 104 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, New York WIMAX is a registered trademark of WiMax Forum, of Beaverton, Oregon BLUETOOTH is a registered trademark of Bluetooth SIG, Inc. of Kirkland, Washington Although illustrated collocated with the sensing system 102, the computing device 104 may be located remote from the sensing system 102, and may include a cloud computing device, a distributed computing device, or any other suitable computing device. Moreover, more than one computing device 104 may be used to perform the actions described herein.

System 100 also includes a data management system 108 that is coupled to computing device 104 via a network 109. Data management system 108 may be any device capable of accessing network 109 including, without limitation, a desktop computer, a laptop computer, or other web-based connectable equipment. The data management system 108 may be, or be part of, a PACS. More specifically, in the exemplary embodiment, data management system 108 includes a database 110 that includes previously acquired data of other subjects. In the exemplary embodiment, database 110 can be fully or partially implemented in a cloud computing environment such that data from the database is received from one or more computers (not shown) within system 100 or remote from system 100. Database 110 can also include any additional information of each of the subjects that enables system 100 to function as described herein.

Data management system 108 may communicate with computing device 104 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 108 transmits the data for the subjects to computing device 104. While the data is shown as being stored in database 110 within data management system 108, it should be noted that the data of the subjects may be stored in another system and/or device. For example, computing device 104 may store the data therein.

Figure 1B:
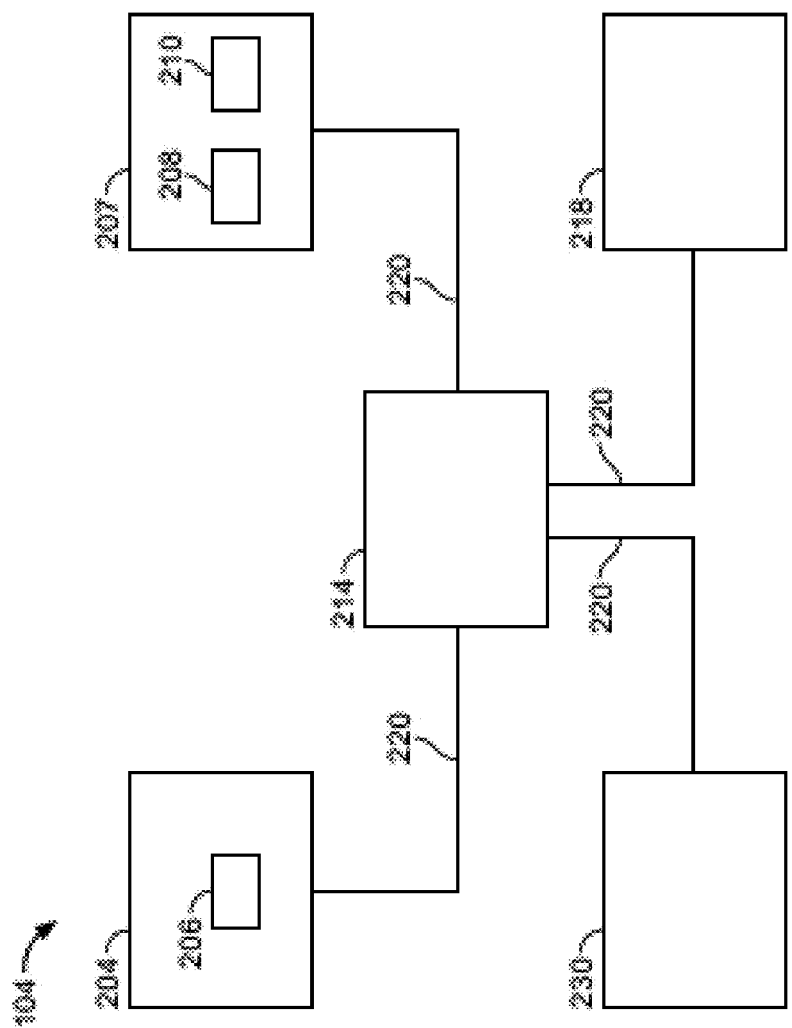
FIG. 1B is a block diagram of an exemplary computing device in the exemplary system shown in FIG. 1A.

FIG. 1B is a block diagram of computing device 104, which again, as discussed above, may represent multiple different computing systems performing different functions (e.g., controlling the RS-fMRI image acquisition, performing the functional mapping processing on acquired RS-fMRI data, and performing image communication and archiving functions). In the exemplary embodiment, computing device 104 (and each of multiple different computing systems represented by device 104) includes a user interface 204 that receives at least one input from a user, such as an operator of sensing system 102 (shown in FIG. 1A). User interface 204 may include a keyboard 206 that enables the user to input pertinent information. User interface 204 may also include, for example, a pointing device, a mouse, a stylus, a touch sensitive panel (e.g., a touch pad, a touch screen), a gyroscope, an accelerometer, a position detector, and/or an audio input interface (e.g., including a microphone).

Moreover, in the exemplary embodiment, computing device 104 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 104 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 104, in the exemplary embodiment, may also include a communication interface 230 that is coupled to processor 214 via system bus 220. Moreover, communication interface 230 is communicatively coupled to sensing system 102 and to data management system 108 (shown in FIG. 1A).

In the exemplary embodiment, processor 214 may be programmed by encoding an operation using one or more executable instructions and providing the executable instructions in memory device 218. In the exemplary embodiment, processor 214 is programmed to select a plurality of measurements that are received from sensing system 102 of brain activity that is representative of at least one parameter of the brain of the subject during a resting state. The plurality of measurements may include, for example, a plurality of voxels of at least one image of the subject's brain, wherein the image may be generated by processor 214 within computing device 104. The image may also be generated by an imaging device (not shown) that may be coupled to computing device 104 and sensing system 102, wherein the imaging device may generate the image based on the data received from sensing system 102 and then the imaging device may transmit the image to computing device 104 for storage within memory device 218. Alternatively, the plurality of measurements may include any other type measurement of brain activity that enables system 100 to function as described herein.

Processor 214 may also be programmed to perform a correlation analysis. More specifically, in the exemplary embodiment, processor 214 may be programmed to compare at least one data point from each of the plurality of measurements with a corresponding data point from a previously acquired data set from at least one other subject. For example, processor 214 may be programmed to compare a resting state data point from each selected voxel from an image of the subject with a corresponding data point that is located within the same voxel of the previously acquired data set of the other subject. Processor 214 may also be programmed to produce at least one map (not shown in FIG. 1B) of the brain of the subject, such as a functional connectivity map, for each of the plurality measurements.

Processor 214 may also be programmed to categorize or classify the measured brain activity in a plurality of networks in the brain based on the map. For example, processor 214 may be programmed to categorize the measured brain activity to a particular neural network of the brain of the subject based on the location of the measured brain activity on the map of the subject's brain.

During operation, as the subject is in a resting state, sensing system 102 detects a plurality of measurements of brain activity that is representative of at least one parameter of the brain of the subject. Sensing system 102 transmits at least one signal representative of the measurements to computing device 104 via data conduit 106. More specifically, the signals are transmitted to and received by communication interface 230 within computing device 104. Communication interface 230 then transmits the signals to processor 214 for processing and/or to memory device 218, wherein the data may be stored and transmitted to processor 214 at a later time. Processor 214 may generate an image of the plurality of measurements. Alternatively, sensing system 102 may transmit the signals to an imaging device (not shown), wherein an image of the measurements may be generated. The image may then be transmitted to computing device 104, wherein the image is stored within memory device 218 and transmitted to processor 214 for processing.

Moreover, data of other subjects may be transmitted to computing device 104 from database 110 (shown in FIG. 1A) via network 109 (shown in FIG. 1). More specifically, the data may be received by communication interface 230 and then transmitted to processor 214 for processing and/or to memory device 218, wherein the data may be stored and transmitted to processor 214 at a later time. Computing device 104 may obtain the data at any time during operation.

In the exemplary embodiment, computing device 104 produces at least one map for each of the plurality of measurements received. More specifically, processor 214 first selects each of the plurality of measurements, received from sensing system 102. For example, in the exemplary embodiment, processor 214 selects each of the volume elements (voxels) from the image. Alternatively, processor 214 may select any other types of measurements for brain activity that enables system 100 to function as described herein. Moreover, a user may see the image on the computing device 104, via presentation interface 207, and select the measurements, such as voxels, via user interface 204.

When each of the measurements has been selected, processor 214 then performs a correlation analysis. More specifically, processor 214 compares at least one data point from each of the selected measurements with a corresponding data point from a previously acquired data set from at least one other subject, wherein computing device 104 obtained the data set from database 110. For example, processor 214 may compare at least one resting state data point from each selected voxel of the image of the subject with a data point that is located within the same voxel of the previously acquired data set of at least one other subject.

When processor 214 has completed the correlation analysis, processor 214 then produces at least one map (not shown in FIG. 2) of the brain of the subject, such as a functional connectivity map, for each of the measurements. More specifically, processor 214 produces a map of the brain of the subject based on each of the comparisons of each of the resting state data points and the corresponding previously acquired data points. The map, for example, may illustrate the location within the brain of a measured brain activity. Processor 214 then categorizes or classifies the measured brain activity in a plurality of networks in the brain based on the map. For example, based on the location of the measured brain activity in the map, processor 214 categorizes the measured brain activity to a particular neural network of the brain of the subject. The map may be presented to the user via presentation interface 207. Moreover, a textual representation and/or a graphical output for the various categorizations may also be presented to the user via presentation interface 207.

Figure 2A:
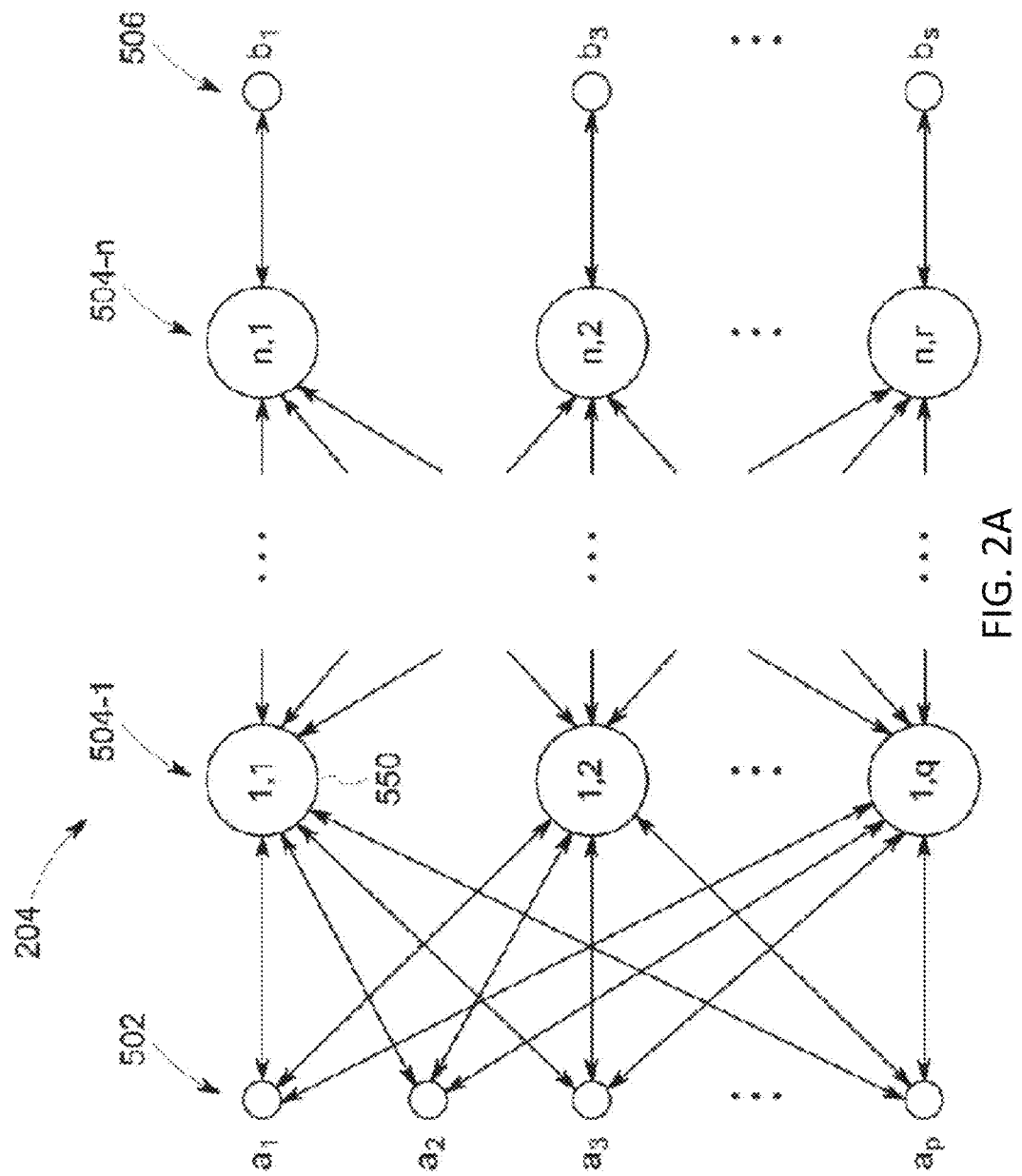
FIG. 2A is a schematic diagram of a neural network model.

FIG. 2A depicts an exemplary artificial neural network model 204 used in the systems and methods described above. The exemplary neural network model 204 includes layers of neurons 502, 504-1 to 504-$n$, and 506, including an input layer 502, one or more hidden layers 504-1 through 504-$n$, and an output layer 506. Each layer may include any number of neurons, i.e., q, r, and n in FIG. 1A may be any positive integers. It should be understood that neural networks of a different structure and configuration from that depicted in FIG. 2A may be used to achieve the methods and systems described herein.

In the exemplary embodiment, the input layer 502 may receive different input data. For example, the input layer 502 includes a first input $a_1$ representing training images, a second input $a_2$ representing patterns identified in the training images, a third input $a_3$ representing edges of the training images, and so on. The input layer 502 may include thousands or more inputs. In some embodiments, the number of elements used by the neural network model 204 changes during the training process, and some neurons are bypassed or ignored if, for example, during execution of the neural network, they are determined to be of less relevance.

In the exemplary embodiment, each neuron in hidden layer(s) 504-1 through 504-$n$ processes one or more inputs from the input layer 502, and/or one or more outputs from neurons in one of the previous hidden layers, to generate a decision or output. The output layer 506 includes one or more outputs each indicating a label, confidence factor, weight describing the inputs, and/or an output image. In some embodiments, however, outputs of the neural network model 204 are obtained from a hidden layer 504-1 through 504-$n$ in addition to, or in place of, output(s) from the output layer(s) 506.

In some embodiments, each layer has a discrete, recognizable function with respect to input data. For example, if n is equal to 3, a first layer analyzes the first dimension of the inputs, a second layer the second dimension, and the final layer the third dimension of the inputs. Dimensions may correspond to aspects considered strongly determinative, then those considered of intermediate importance, and finally those of less relevance.

In other embodiments, the layers are not clearly delineated in terms of the functionality they perform. For example, two or more of hidden layers 504-1 through 504-$n$ may share decisions relating to labeling, with no single layer making an independent decision as to labeling.

Figure 2B:
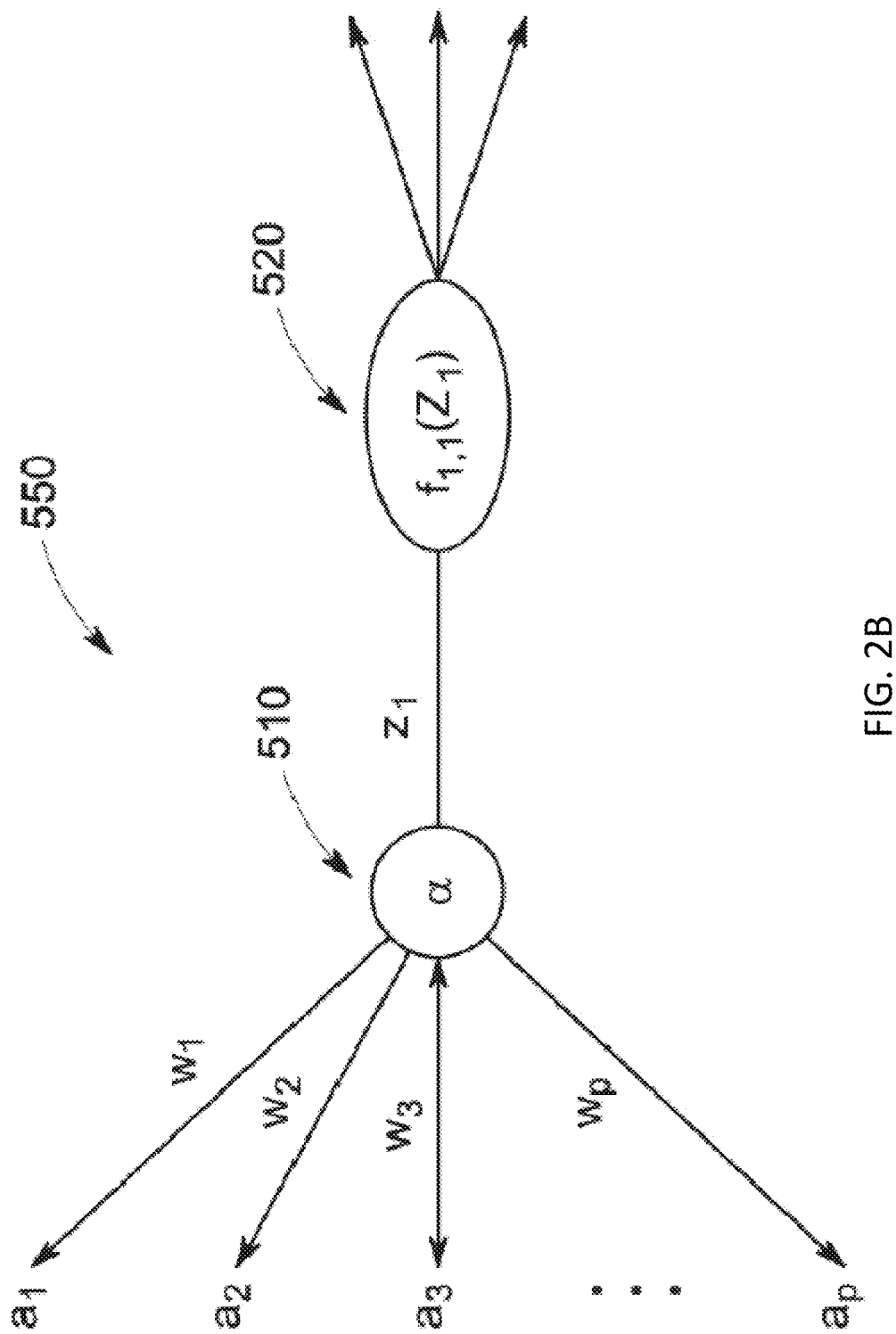
FIG. 2B is a schematic diagram of a neuron in the neural network model shown in FIG. 2A.

FIG. 2B depicts an example neuron 550 that corresponds to the neuron labeled as "1,1" in hidden layer 504-1 of FIG. 2A, according to one embodiment. Each of the inputs to the neuron 550 (e.g., the inputs in the input layer 502 in FIG. 1A) is weighted such that input $a_1$ through $a_p$ corresponds to weights $w_1$ through $w_p$ as determined during the training process of the neural network model 204.

In some embodiments, some inputs lack an explicit weight, or have a weight below a threshold. The weights are applied to a function a (labeled by a reference numeral 510), which may be a summation and may produce a value $z_1$ which is input to a function 520, labeled as $f_{1,1}(z_1)$. The function 520 is any suitable linear or non-linear function. As depicted in FIG. 2B, the function 520 produces multiple outputs, which may be provided to neuron(s) of a subsequent layer, or used as an output of the neural network model 204. For example, the outputs may correspond to index values of a list of labels, or may be calculated values used as inputs to subsequent functions.

It should be appreciated that the structure and function of the neural network model 204 and the neuron 550 depicted are for illustration purposes only, and that other suitable configurations exist. For example, the output of any given neuron may depend not only on values determined by past neurons, but also on future neurons.

The neural network model 204 may include a convolutional neural network (CNN), a deep learning neural network, a reinforced or reinforcement learning module or program, or a combined learning module or program that learns in two or more fields or areas of interest. Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. The neural network model 204 may be trained using unsupervised machine learning programs. In unsupervised machine learning, the processing element may be required to find its own structure in unlabeled example inputs. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics, and information. The machine learning programs may use deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Based upon these analyses, the neural network model 204 may learn how to identify characteristics and patterns that may then be applied to analyzing image data, model data, and/or other data. For example, the model 204 may learn to identify features in a series of data points.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

EXAMPLES

Example 1: Integrative and Network-Specific Connectivity of the Basal Ganglia and Thalamus Defined in Individuals I. Introduction MRgRT with an integrated MRI and radiotherapy delivery system provides onboard imaging with excellent soft-tissue contrast without additional radiation exposure, enabling real-time tumor tracking, and the capability to perform online adaptive radiation therapy (ART). Online ART utilizes on-table 3D MRI scans to adapt an original treatment plan to the current anatomy of the patient which may have changed due to setup errors, anatomical changes such as weight loss, and changes in tumor size. ART significantly improves the dose calculation and radiation delivery accuracy, resulting in reduced dose to surrounding tissue and improved local control of disease. Integrated MRI and radiation delivery systems such as MR-linacs may also provide real time cine MRI for target tracking during treatment delivery to provide beam gating, resulting in further improvements in local tumor control and normal tissue toxicity.

Current onboard MRI systems face the problem of limited spatial resolution related inversely to scanning time, especially on low-field MRI systems (<1.5 T). To obtain high-resolution MR images multiple changes may be made to acquisition parameters including: increased acquisition time, narrowing the field of view, and reducing the signal-to-noise ratio (SNR). However, increasing image acquisition time may increase the presence of motion blurring, narrowed field of view limits the dose calculation volume, and reduced SNR may prevent anatomical structure identification. In MRgRT, the resolution of the MRI fundamentally determines setup uncertainty, the accuracy of target definition, and tracking precision. Therefore, scan time should be minimized while maximizing the spatial resolution of the MRI. This is especially true for target tracking with cine MRI, which requires the acquisition of multiple images every second to provide adequate tracking accuracy due to the period, amplitude, and irregularity of respiratory motion. Currently, the ViewRay MR-linac provides 4 frames per second (fps) 2D cine acquisitions in the sagittal plane with 3.5 mm pixel edge, and 8 fps acquisition with a 2.4 mm pixel edge utilizing a data sharing method, and a slice thickness of 5, 7, or 10 mm. The 8 fps method provides higher spatiotemporal resolution but the data sharing method introduces image blurring. These images sacrifice a significant level of spatial resolution, edge sharpness, and SNR to achieve sufficient temporal resolution, which impacts the performance of automatic tracking algorithms and target boundary identification.

Previous works have shown that the spatial resolution of MRI may be greatly improved without changing hardware or scanning parameters by utilizing imaging postprocessing techniques known as super-resolution (SR). The purpose of the SR reconstruction is to restore high-resolution (HR) image information only using low-resolution (LR) images.

A robust SR volumetric MRI reconstruction framework uses a novel cascaded DL approach. The feasibility assessment for volumetric MRI was conducted based on MRI scans acquired from healthy volunteers. This is the first application of the SR MRI reconstruction framework for clinical 2D cine MRI. This study extends further to evaluate the performance of SR MRI reconstruction to generate SR 2D images from a unique data set of cine MRI scans from 50 pancreatic cancer patients acquired on the ViewRay MR-linac prior to clinical implementation.

II. Methods and Materials

II.A. Super Resolution Framework

The SR framework was developed for in-plane SR reconstruction slice by slice and resolution in the out-of-plane direction remained unchanged. This allowed the application of the method to 2D cine MRI.

II.B. Data Acquisition

All data used in this study was acquired on the ViewRay MRIdian MRgRT system (ViewRay Inc., Oakwood Village, Ohio), which integrates a split-bore 0.35 T whole-body MRI system with a linac based radiation therapy system. MRIs of the patients were acquired in clinical mode using anterior and posterior torso phased-array receiver coils over the course of five fraction adaptive stereotactic-body radiation therapy (SBRT). For evaluation, a dataset of 50 consecutive pancreatic cancer patients treated on the ViewRay MRIdian system was retrospectively collected. Each patient had sagittal 2D cine MRI data sets acquired during treatment (LR images) with the following parameters: TR=2.1 ms, TE=0.91 ms, flip angle=60°, FOV=350×350 $mm^2$, voxel size=3.5×3.5 $mm^2$, slice thickness=7.0 mm, readout bandwidth=1351 Hz/Px, phase partial Fourier=6/8. A 3D volumetric image was also acquired for online adaptive planning (HR images) with the following parameters: TR=3.33 ms, TE=1.43 ms, flip angle=60°, FOV=400×400 $mm^2$, voxel size=1.5×1.5 $mm^2$, slice thickness=3.0 mm, readout bandwidth=537 Hz/Px, phase partial Fourier=6/8.

II.C. Intrinsic Metrics for Image Quality Evaluation

Super resolution (SR) images generated from LR cine MRI images were evaluated using intrinsic metrics and compared to the scores from the original LR cine MRI images. Three different metrics were calculated using MATLAB (version R2020b, MathWorks). The metrics included: blind/referenceless image spatial quality evaluator (BRISQUE), natural image quality evaluator (NIQE), and perception based image quality evaluator (PIQE). All three metrics generate a score from 0 to 100 to indicate the naturalness, presence of distortion, and noise level of an image, with 0 representing an excellent quality image. Evaluation was performed on a single fraction for all 50 pancreatic cancer patients and a total of 24,000 images.

II.D. Relative Metrics for Image Quality Evaluation

Super resolution (SR) images were evaluated using both qualitative and quantitative methods against the LR images for relative image metrics in MATLAB. Qualitative evaluation utilized extracting edges and comparing the overlap of the detected edges to confirm structures were not created or significantly distorted. The quantitative assessment used the structural similarity index (SSIM). To perform SSIM between LR and SR images, LR images were upsampled to match the SR images and SR images were downsampled to match LR images, by 4-fold and, using nearest neighborhood and bilinear algorithms. The intensity gradient of the anterior abdominal wall on LR and SR images was compared to evaluate edge sharpness.

An additional SSIM evaluation was performed for LR and SR images versus the original slices of HR 3D images. Evaluation was performed on all 50 pancreatic cancer patients and a total of 24,000 images.

II.E. Tumor Contour for Clinical Quality Evaluation

Tumor contours were generated with inhouse software developed in MATLAB on LR and SR cine image sets, using the original autocontour generated by the ViewRay system as the starting point. This goal of this test was not to test the accuracy of the generated contour, but to assess the impact of high noise LR and SR images on a contouring algorithm that is readily available. The similarity between the LR and SR contours were compared using DICE similarity coefficient and shape similarity coefficient. To investigate the robustness of contour generation on LR and SR images, gaussian noise was added to the images at different variance levels, from 0 to 0.04, and a mean value of 0.

III. Results

III.A. Intrinsic Metrics for Image Quality Evaluation

Figure 3:
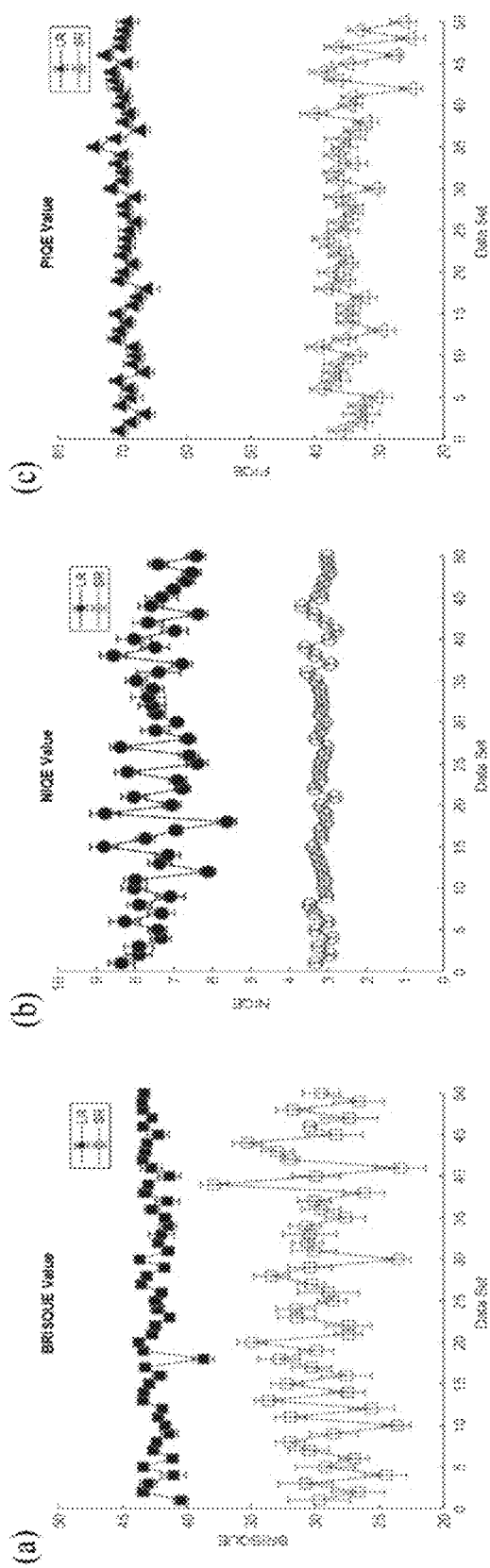
FIG. 3 depicts three intrinsic metrics for 50 patients calculated for the low resolution and super resolution images.

Three intrinsic metrics for all 50 patients and are shown in FIG. 3. Intrinsic metrics are calculated for the low resolution (LR, blue) and super resolution (SR, red) images, including (a) blind/referenceless image spatial quality evaluator (BRISQUE), (b) naturalness image quality evaluator (NIQE), and (c) perception based image quality evaluator (PIQE). All three metrics generate a score from 0 to 100 to indicate the naturalness, presence of distortion, and noise level of an image, with 0 representing an excellent quality image. SR images scored a mean (±1 SD) of 29.65±2.98 for BRISQUE, 3.17±0.18 for NIQE, and 34.58±3.38 for PIQE. LR images scored a mean (±1 SD) of 42.48±0.98 for BRISQUE, 7.40±0.69 for NIQE, and 69.46±1.52 for PIQE. SR images performed significantly better for all three metrics (p-value<<0.05).

Figure 4:
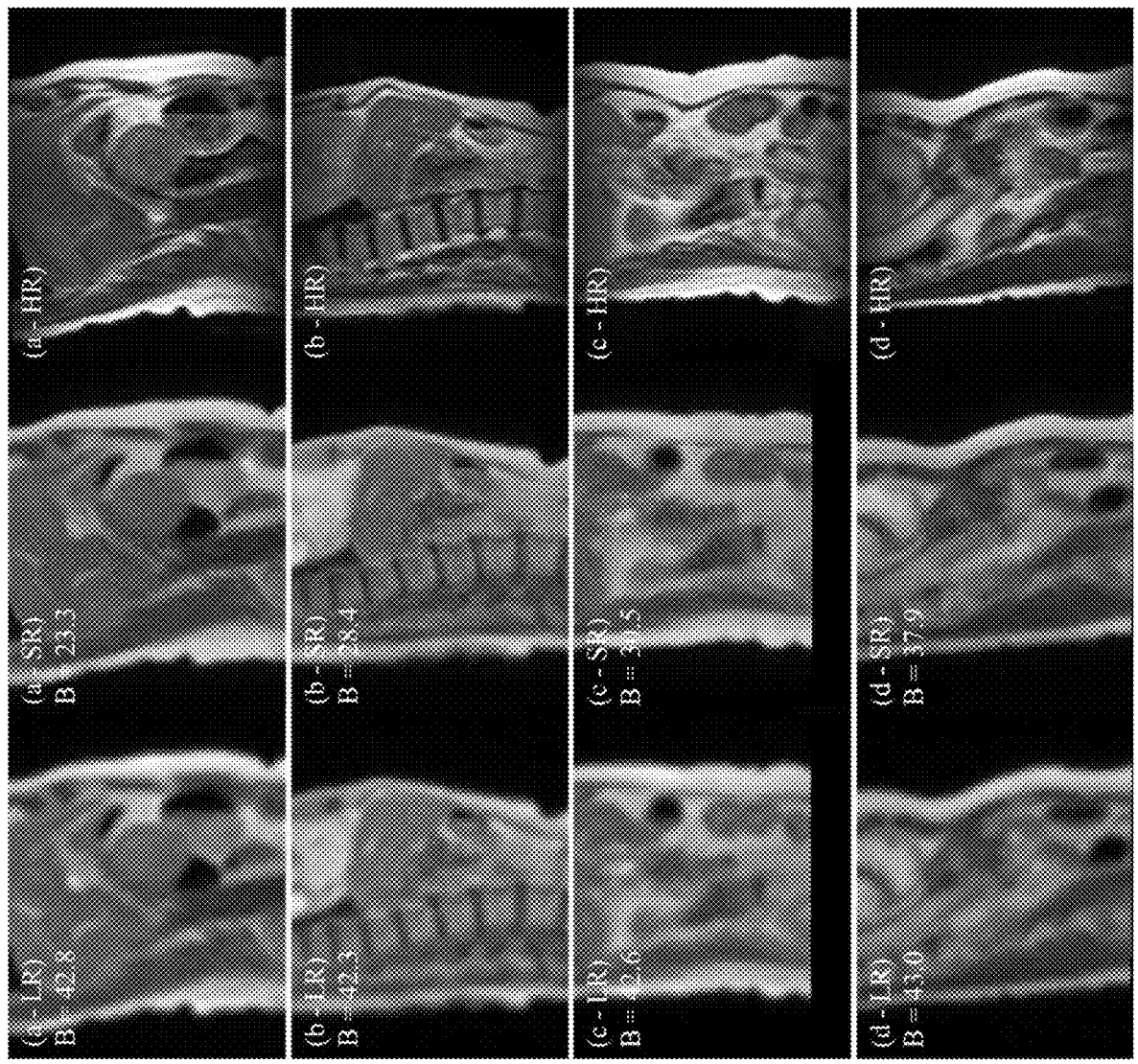
FIG. 4 depicts low resolution, super resolution

FIG. 4 shows the LR and SR images and the paired 3D high resolution (HR) image for the patients with the $1^{st}$ (best), $33^{rd}$, $66^{th}$, and $100^{th}$ (worst) percentile BRISQUE value from SR images, where $1^{st}$ percentile indicates the best and $100^{th}$ percentile indicates the worst BRISQUE ratings. The B value is the mean BRISQUE value for the patient. The figure represents the range of observed intrinsic quality metrics calculated for SR images. LR images had a resolution of 3.5×3.5 mm$^2$ while SR images had a resolution of 0.875×0.875 mm$^2$. Total computational time for generating SR images was 0.3 ms/slice. Predicted acquisition time for SR images with conventional acquisition is 1 second.

III.B. Relative Metrics for Image Quality Evaluation

Structural similarities between SR and LR images were evaluated qualitatively and quantitatively to verify the reliability of the SR model. FIGS. 5A-5H show the qualitative results of structural similarity evaluation. FIG. 5A is an LR (100×100 pixels, 3.5×3.5 mm$^2$ resolution) image, FIG. 5B is an SR (400×400 pixels, 0.875×0.875 mm$^2$ resolution) image of FIG. 5A, FIG. 5C is an overlaid image of FIGS. 5A and 5B, FIG. 5D is an overlapped image of FIGS. 5C and 5H, FIG. 5E shows extracted edge of FIG. 5A, FIG. 5F is extracted edge of FIG. 5B; FIG. 5G is an overlaid image of FIGS. 5E and 5F; FIG. 5H is result of logical 'AND' calculation of FIGS. 5E and 5F. The edge maps are overlayed in FIG. 5G, and the overlapping edges are shown in FIG. 5H. This information may be expressed in overlaid images of LR and SR images, shown in FIG. 5C to qualitatively confirm that SR models do not create new structures or distort existing structures (see FIG. 5D).

Quantitative evaluation with SSIM showed very high similarity between LR and SR pairs. LR images upsampled to the SR image resolution had mean (±SD) SSIM values of 0.77±0.02 and 0.82±0.02 for nearest neighbor and bilinear interpolation methods. SR images downsampled to the LR image resolution had mean (±SD) SSIM values of 0.84±0.02 and 0.88±0.02 for nearest neighbor and bilinear interpolation methods. Evaluation of LR and SR images versus HR images with SSIM showed that SR images had a statistically significant improvement (p>>0.05) in SSIM values, shown in FIGS. 6A-4C.

FIG. 6A displays the SSIM values for comparison of low resolution (LR) images that have been upsampled to the resolution of super resolution (SR) images. FIG. 6B displays the SSIM values for comparison of SR images that have been downsampled to the resolution of LR images. FIG. 6C displays SSIM values for LR and SR images with the paired high resolution (HR) image as reference for each patient. Error bars indicate 1 standard deviation.

FIGS. 7A-5D are line profiles drawn along the yellow dotted line of FIGS. 5A and 5B of LR and SR images for four different patients with different BRISQUE ratings including the best (FIG. 7A), $33^{rd}$ percentile (FIG. 7B), $66^{th}$ percentile (FIG. 7C), and worst (FIG. 7D). The Blue dotted line indicates the line profile of the LR image and the red solid line indicates that of SR image. The vertical dashed lines indicate the region that the abdominal wall intensity slope was measured at. The gradient of SR images was 17.71±3.17, more than 23% steeper than the gradient of 14.39±3.51 for LR images, and the p-value (p<<0.05) showed statistically significant differences in a t-test.

III.C. Tumor Contour for Clinical Quality Evaluation

Figure 8A:
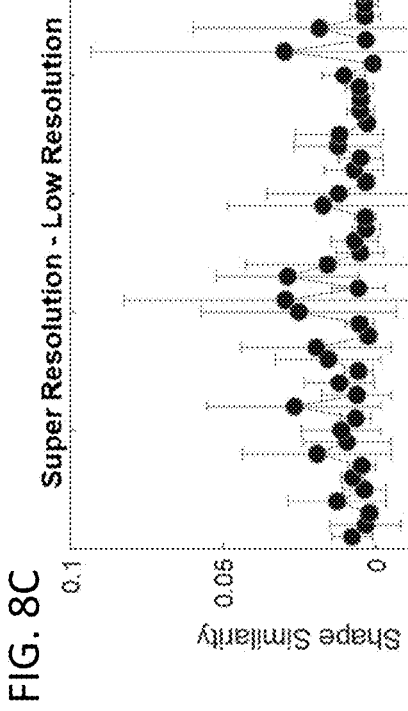
Figure 8B:
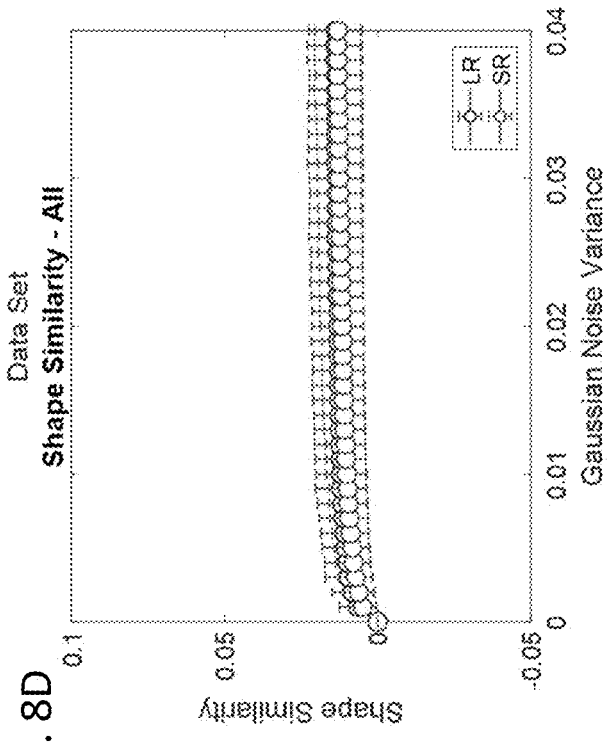
Figure 8C:
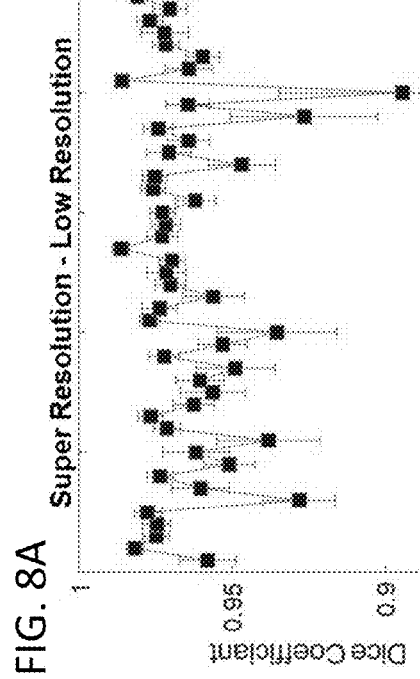
Figure 8D:
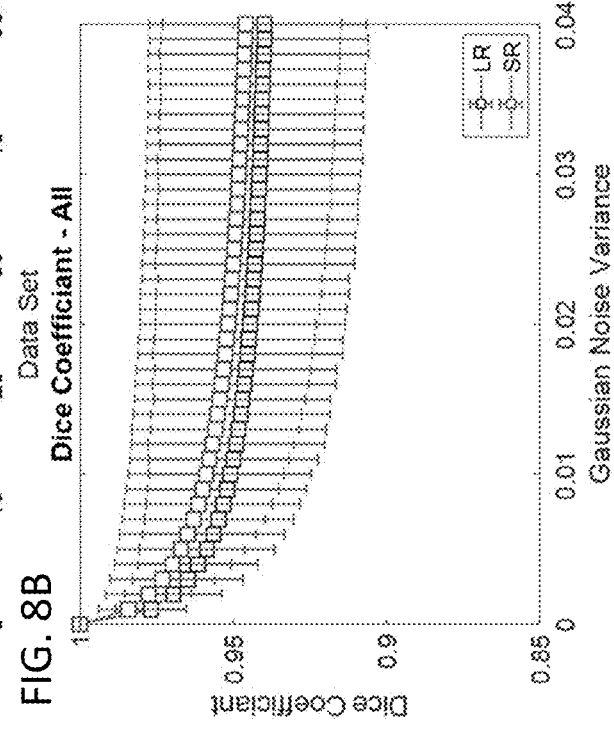

Evaluation of tumor contours with shape similarity coefficient and DICE coefficient showed high similarity between LR and SR contours with no noise added, for 49 out of 50 patients. The exception was patient 40 which had a low quality initial contour. The addition of gaussian noise indicated that the SR images were more robust to noise than the LR images. FIGS. 8A-6D show the shape similarity and DICE coefficients for all 50 patients and the change in these metrics with the addition of noise. FIGS. 8A and 8B show the average, with 1 standard deviation, dice coefficient and shape similarity coefficient, respectively, between LR and SR contours for each data set. FIGS. 8C and 8D show the average, with 1 standard deviation, dice coefficient and shape similarity coefficient, respectively, for LR and SR images with gaussian noise added at different variance levels.

FIGS. 9A-9D show the LR and SR images with and without added noise for the patients that had the worst and best DICE scores. The patients with the $1^{st}$ (FIG. 9A), $33^{rd}$ (FIG. 9B), $66^{th}$ (FIG. 9C), and $100^{th}$ (FIG. 9D) percentile BRISQUE value from SR images are shown. The original low resolution (LR) cine images (first column), LR image with gaussian noise added (second column), super resolution images (SR) cine images (third column), and SR images with gaussian noise added (fourth column) are shown. The gaussian noise was added with a variance of 0.02 and a mean of 0. The green contour is the original contour from the MRgRT system and the red contour is generated by in-house software.

IV. Discussion

In this study, the super resolution framework was applied to low resolution cine MRI images acquired on a 0.35 T MRgRT system for 50 pancreatic cancer patients. This work showed that the super resolution framework was able to improve image resolution from 3.5 mm to 0.9 mm without introducing new structures or significant deformation to the images. Additionally, the tumor contours were similar between LR and SR images, but contour generation on SR images was more robust to addition of gaussian noise and SR images provided sharper edges between tissue. This shows promising clinical utility for real-time application during target tracking and beam gating, and improved visual target identification for clinicians.

One of the major limitations of MRgRT is the limitation of image resolution due to image acquisition time. The super resolution framework used in this study allows for quickly generating super resolution images from 2D cine images acquired at 4 frames per second (FPS). The increased resolution allows for improved structure identification and automatic contour generation. The framework is trained with an extensive set of matched pairs of low and high resolution images. The downsampling model used for this work was able to generate accurate downsampled images from original high resolution images that are regularly acquired during MRgRT. This downsampling model allows for more accessible SR model training.

This work is the first application of the SR reconstruction framework to clinical 2D cine MRI images acquired on an MR-linac, and utilizes a unique data set of 50 pancreatic cancer patients.

V. Conclusion

Super resolution 2D images were generated from low resolution 2D cine MRI acquired during MRgRT using a machine learning based super resolution framework. The super resolution images showed no distortion of internal structures and had good agreement with paired high resolution images acquired on the MR-Linac immediately before treatment. Contours generated on super resolution images were more robust to noise than on low resolution images. This method provides fast super resolution images that may be used in the clinical work flow for real time MRgRT and beam gating.

The application of SR techniques to 2D cine MRI used for real time target tracking may have significant improvements in the quality of tracking and beam gating. The resolution improvement provided by SR may make it possible to acquire sufficient 8 fps 2D cine MR images without view sharing, significantly reducing edge blurring and beam gating latency. The faster acquisition speed make sudden motion events, such as coughes or gas motion in the abdomen, easier to observe and improve beam gating in these cases as well.

Example 2: Deep-Learning Framework Applied to 2D Cine MR Images

In one embodiment, a previously trained deep-learning framework is applied to 2D cine MR images acquired during MRgRT of 50 pancreatic cancer patients. A total of 24,000 cine MR images were analyzed, with 480 images obtained from each patient. In future embodiments, there may be integration of the SR system into the clinical MRgRT environment where it will be tested for beam gating and target tracking in real time.

SR images have improved intrinsic and relative image quality and similarity metrics when compared to the original LR images. FIG. 10 shows the SR and LR images from four different patients, which have increasing SR BRISQUE values from left to right: 23.34, 28.40, 30.47, and 37.91. Smaller BRISQUE values indicate better image quality.

FIG. 11A depicts low, super, and 3D high resolution paired images from one patient, FIG. 11B depicts BRISQUE values for all patients, and FIG. 11C depicts SSIM values for all patients compared to paired high resolution 3D images.

Example 3: Amplified-Resolution MRI-Guided Radio Therapy (AR-MRgRT)

Abstract

Current low-resolution cine MRI-guidance can be suboptimal in MRI-guided radiotherapy (MRgRT) due to uncertainty in the real-time target delineation and tracking. Imprecise tumor tracking can lead to mistargeting the tumor and irradiating healthy surrounding tissues, resulting in an increase in radiation-related toxicity.

In one embodiment, amplified-resolution (AR) cine MRI is generated using deep-learning for real-time MRgRT. Low-resolution cine MRI is input to a reconstruction framework built using deep-learning techniques for amplifying image resolution. This embodiment is implemented in the clinical setup to evaluate the clinical feasibility in terms of real-time data transfer, image generation and display. In addition, assessments in virtual clinical setups are conducted to characterize AR-MRgRT in terms of target tracking and gating latency.

The embodiment provides optimal tumor motion monitoring tools in real-time MRgRT, resulting in a decrease in healthy tissue toxicity and an increase in local disease control.

Background

MRI-guided radiotherapy (MRgRT) is a highly desirable treatment modality for delivering image-guided radiation treatment to patients because it combines the superior soft tissue contrast of patient anatomy provided by real-time MRI without the ionizing radiation imparted by X-ray imaging. MRgRT treatments have demonstrated excellent local control rates with little toxicity.

MRI-guided adaptive radiotherapy (MRgART) is one of the most distinguishing and rapidly evolving treatment technologies for thoracic and abdominal cancers. MRgART centers on treatment adaptation over time to compensate for changes in patient anatomy and the tumor in order to deliver a higher quality treatment. Inter-fractional changes of patient anatomy can be managed by online adaptive planning on daily high-resolution MRI (3D MRI). Also, intrafractional adaptation to tumor changes can be achieved using real-time MRI-guided delivery (cine MRI). Outstanding imaging is required to characterize anatomical changes, provide comprehensive motion management to monitor target changes and ensure efficient treatment delivery to maximize the benefits provided by adaptation.

Rationale

Outstanding imaging is a key component in precise and effective MRgART. Two key imaging components are 1) 3D anatomical MRI for precise adaptive planning and 2) real-time cine MRI for precise and effective beam delivery. One of the key problems to be solved in this proposal is presented in the schematic of amplified-resolution cine MRI in MRgART on ViewRay MRidian in FIG. 12.

FIG. 12 is a schematic of the example embodiment: a) Cine MRI on the TDS display at the treatment console is captured using a frame grabber which is input to the SR reconstruction computer for real-time SR image generation and display in addition to the captured clinical MRgRT images (Step-II), b) AR-cine MRIs of the motion phantom is fed into MR-LINAC treatment control/Syngo computers for virtual target-tracking and beam-gating (Step-III).

Low-Quality High-Resolution 3D Anatomical MRI

Currently, 3D anatomical MRI used in ViewRay MRgART has 1.5×1.5×3 mm3 imaging resolution (acquisition time: 17 s/volume). Although the apparent image resolution is comparable to those of clinical MR simulators (1.5 T or 3 T), quality of MR images are substantially inferior to those produced by clinical MR simulators due to low magnetic field strength (0.35 T). Which can lead to inaccurate target and organ delineations during online adaptive planning shown in FIG. 13.

FIG. 13 depicts liver MRIs. a) MRIs from 1.5 T Philips MRI and b) MRIs from ViewRay MR-LINAC (0.35 T). Axial 3D MRI: ViewRay MRI has an apparent image resolution comparable to the 1.5 T MR simulator, but quality of MRI is substantially inferior to the 1.5 T MR simulator due to low magnetic field strength (0.35 T). The liver tumor is not visible on ViewRay MRI (blue arrow), in contrast to MR simulator (green arrow). Sagittal 2D cine MRI: Since the liver tumor is not visible on ViewRay MRI, the whole liver, instead of liver tumor, is used for beam gating. Which can lead to inaccurate targeting. Yellow: reference target contour, Red: temporal target contour.

Low-Quality Low-Resolution 2D Cine MRI 2D cine MRI is fully utilized for real-time continuous tumor motion management during the treatment delivery. Cartesian 4 frame per second (FPS) cine MRI with low-resolution (3.5×3.5 mm2) has been used for target tracking and beam gating (250 ms/frame). It serves as the basis for motion tracking in real-time but low-quality low-resolution cine MRI hinders precise target tracking, shown FIG. 13(b). After a system upgrade, radial 8 FPS cine MRI with 2.4×2.4 mm2 resolution is available (full data acquisition: 500 ms/frame, image display: 125 ms/frame) but introduces artifacts related to the data sharing reconstruction in return. The impact of the artifacts has not been evaluated in clinical setup.

Specific Aims

Hypothesis: Amplified-resolution cine MRI will improve tumor motion management by increasing tumor tracking accuracy and gating efficiency in real-time MRgRT.

The following studies are performed:

Specific Aim 1. Developing amplified-resolution cine MRI in MRgRT:

SA1-I: Developing amplified-resolution cine MRI using deep-learning on MRgRT (AR-MRgRT)

SA1-II: Implementing AR-MRgRT in a clinical setup

SA1-III: Evaluating target tracking accuracy and gating efficiency with AR-MRgRT in a virtual clinical setup.

Preliminary Results and Research Plan

Preliminary Results

Amplified-resolution 3D MRI: The feasibility of amplified-resolution 3D/4D MRI in MRgRT, such as deep-learning-based super-resolution MRI and data-sharing-based dynamic keyhole high-resolution MRI is reported. The studies demonstrated the spatiotemporal resolution of MRI can be greatly improved without changing hardware or scanning parameters by utilizing image post-processing techniques. FIG. 14 shows (a) 3D super-resolution (SR) MRI on coronal plane and (b) 2D SR cine MRI on sagittal plan using off-line reconstruction and post-processing. However, clinical evaluation of the proposed techniques in MRgRT has not been fulfilled due to the off-line setting of previous work. The proposed study extends further to clinically evaluate the performance of SR cine MRI reconstruction in an online clinical MRgRT setup.

FIG. 14. (a-b) Super-resolution MRI reconstruction (SR) from low-resolution measurements (LR) using deep-learning technique: offline reconstruction and post-processing. (a) Coronal 3D MRI and (b) sagittal 2D cine MRI. (c) MRI4D QUASAR motion phantom and imaging cuboid for beam gating quantification. The phantom installed on the phantom rack mounted on the couch top, cine MRI of the phantom in a sagittal plane with beam gating boundary (red) and gating target (yellow), and beam gating signal received from LINAC control system.

MR-LINAC characterization: Accuracy of treatment when real-time targeting and gating is enabled depends on the gating processes including imaging, target tracking and radiotherapy machine control. MR-LINAC characterization is a key procedure to quantify the efficacy of target-tracking and beam gating in MRgRT. Recently, we developed pioneering procedures for MR-LINAC characterization, such as beam gating latency, MRI isocenter variation, and advanced imaging parameters. FIG. 12 shows an example setup of gating latency quantification, which will be utilized in the proposed project.

Research Plan

Developing amplified-resolution cine MRI in MRgRT: Amplified-resolution (AR) cine MRI will be developed and implemented in a clinical setup of MRgRT. The proposed three step plan is presented below.

Step-I: Developing Amplified-Resolution Cine MRI Using Deep-Learning in MRgRT (AR-MRgRT)

1) The Super-Resolution framework is reestablished) using deep-learning, which allows further improvement in the spatiotemporal resolution of cine MRI.

2) The previous framework of 3D MRI may be utilized. The framework was developed for in-plane SR reconstruction in a slice-by-slice process, which allows the application of the previous framework to 2D cine MRI as an alternative.

Step-II: Implementing AR-MRgRT in Clinical Setup

1) A dual screen output of the TDS system display from the ViewRay MR-LINAC is utilized such that cine MRI on the TDS display at the treatment console will be captured using a signal capturing device (ex: frame grabber).

2) The captured cine MRI is input to the SR reconstruction computer for real-time SR image generation and displayed in addition to the clinical low-resolution cine MR images.

3) Cine MRI capturing by the signal capturing device provides more options in signal processing and less challenges in accessibility than directly obtaining MR images from ViewRay MR-LINAC. It is noted that currently, the MR-LINAC imaging system is not accessible from external computers to capture cine MRI, but future embodiments may allow for access from external computers.

Step-III: Evaluating Target Tracking Accuracy and Gating Efficiency with AR-MRgRT in Virtual Clinical Setup

*An MRI4D QUASAR motion phantom is utilized in the study.

1) Evaluating impact of AR-cine MRIs on target tracking: In this embodiment, (a) evaluate the feasibility of the proposed techniques for target tracking and (b) identify the uncertainty of the target tracking in a clinical MRgRT environment.

a) AR cine MRIs are generated from Step-I and II, and be input to an MR-LINAC Syngo box for virtual target-tracking evaluation. The four available tracking algorithms are run on 2D cine MRIs with and without SR reconstruction to trace target shape and position.

b) Uncertainty is analyzed and quantified in terms of size and position of target-tracking accuracy. Uncertainty of delivered radiation dose will be estimated using clinical delivery setup.

2) Evaluating impact of AR cine MRIs on gating efficiency: Any substantial uncertainty of the gating efficiency can induce a systematic deviation of the delivered dose from the planning dose. The gating efficiency can be affected by the imaging time and quality, accuracy and efficacy of target tracking algorithms, and radiation beam delivery latency. In this embodiment (a) identify gating latency with the proposed cine MRI and (b) quantify the uncertainty of the radiation dose with AR cine MRIs.

a) AR cine MRIs will be fed into the MR-LINAC treatment control computer for virtual beam-gating evaluation. Beam control utilizing the four clinical tracking algorithms are run on 2D cine MRIs with and without SR reconstruction. Beam latency are quantified, including accuracy and efficacy of target tracking algorithms, and radiation beam delivery latency.

b) Uncertainty of delivered radiation dose are estimated and measured using clinical delivery setup.

Potential Outcomes, Problems, and Alternatives

In this embodiment, the AR cine MRI is developed and the clinical value of the proposed technique is evaluated. In the evaluation, the AR cine MR images are fed to the MR-LINAC computational/control system. Alternatively, the clinical evaluation may be run with each component. For example, target tracking accuracy is evaluated using a common tracking algorithm and the results of the AR cine MRI are compared to those with low-resolution cine MRI. In the gating efficacy evaluation, three components are qualified independently for the gating latency: imaging time, accuracy and efficacy of target tracking algorithms, and radiation beam delivery latency. Since target tracking efficacy were quantified in the previous study and the radiation beam delivery latency is an intrinsic parameter, the time related to the image generation is a key component in the gating efficacy evaluation.

Example 4: Super Resolution for Improving 2D Cine-MRI Resolution During MR Guided Radiotherapy Purpose Spatiotemporal resolution of MR images is limited by hardware and acquisition parameters, especially at low magnetic fields where long imaging times are required to improve SNR and feature identification. These factors are vital to target tracking and beam gating during MR-guided radiotherapy (MRgRT). Super resolution (SR) reconstruction with deep-learning frameworks provides the ability to generate SR images from low resolution (LR) images. This study applies the SR framework to 2D cine MRI acquired on an MRgRT system during pancreatic cancer treatment.

Methods

Real time 4 frames-per-second (FPS) cine MR images are collected retrospectively for fifty pancreatic cancer patients treated on the ViewRay MR-linac system. A previously trained super resolution framework was used to generate SR images from the original 3.5×3.5 mm2 pixel images, with a new resolution of 0.9×0.9 mm2. SR images were compared to the original LR using inherent metrics including: NIQE, PIQE, and BRISQUE. Inherent image metrics score from 0 to 100, 0 indicates an ideal image. SR images were also compared to paired high resolution (HR) 3D images using SSIM and anterior wall intensity gradient as a surrogate for edge sharpness.

Results

SR images had statistically significant improvements for inherent metrics, compared to the LR images. SR images scored a mean (±SD) of 3.17±0.18 for NIQE, 34.58±3.38 for PIQE, and 29.65±2.98 for BRISQUE. LR images scored a mean (±SD) of 7.40±0.69 for NIQE, and 69.46±1.52 for PIQE, and 42.48±0.98 for BRISQUE. SR images also had greater SSIM values and sharper line profiles compared to LR images with SSIM of 0.633±0.063 and 0.587±0.067, and gradients of 17.71±3.17 and 14.39±3.51, for SR and LR images, respectively.

Conclusion

Super resolution images provided improved image quality and target identification without introducing artifacts or anatomical inconsistencies. This leads the way for real time SR image generation during MRgRT for target tracking and gating.

Example 5: Evaluating Pancreatic Tumor Motion and Correlation with X-Ray Visible Surrogates on 0.35 T MR-Linac Cine MRI Treatment tolerability is a significant limitation to treatment of pancreatic cancer with radiotherapy due to close proximity with highly radiosensitive organs at risk and respiratory motion necessitating expanded target margins. Further, pancreatic tumors are difficult to visualize on conventional radiotherapy systems. Surrogates are often used to locate the tumor but are often inconsistent and do not provide linear positional relations throughout the respiratory cycle.

Methods and Materials

This embodiment utilizes a retrospective dataset of 45 pancreatic cancer patients treated on an MR-Linac system with cine MRI acquired during every treatment fraction for real-time target tracking. Intra-fraction tumor motion and prediction models are investigated from X-ray visible surrogates. Patient specific motion evaluation and prediction models are generated from 225 cine MRI series acquired during treatment. Linear regression and principal component analysis (PCA) based models are used to predict tumor position from the anterior-posterior (AP) motion of the abdominal surface, the superior-inferior (SI) motion of the diaphragm, or a combination of the two to determine tumor position. Models are evaluated using mean squared error (MSE) and mean absolute error (MAE).

Results

Contour analysis showed that the pancreatic tumor had an average motion range of 7.4±2.7 mm and 14.9±5.8 mm in the AP and SI directions, respectively. The PCA model had MSE of 0.6 mm2 and 1.4 mm2 for the AP and SI directions, respectively, with both surrogates as inputs for the models. When only the abdomen surrogate was used, MSE was 1.3 mm2 and 0.4 mm2 in the AP and SI directions, while it was 0.4 mm2 and 1.3 mm2 when only the diaphragm surrogate was used.

Conclusions

The models were able to accurately calculate the pancreatic tumor position from diaphragm, abdominal, or a combination of both contours within the standard pancreatic cancer target margin expansion, and the process could be readily applied to other disease sites in the abdominothoracic cavity.

Introduction

Target positioning is an essential step for delivering high quality and effective treatment of cancer in radiotherapy. Small variations, on the order of 5 mm, can result in geometric miss of the target and delivering radiation to surrounding healthy tissue. Extensive work has been applied to accurately position patients using immobilization devices, laser alignment systems, and on-board imaging devices. However, even the most painstaking setup measures can be defeated by a moving target. A common source of motion in radiotherapy is respiration, which can result in target displacements of up to 50 mm, especially in the abdominothoracic region. Tumors near the diaphragm experience the greatest extent of this semi-periodic motion, with few bony structures nearby to use as surrogates in x-ray imaging. To improve treatment of these tumors, gating methods have been implemented to only deliver radiation when the tumor, or a surrogate for the tumor, is in a specified position. These methods often introduce their own complications such as uncertainty in the link between external surrogates and the tumor, increased treatment delivery time, patient discomfort, and treatment machines that are unobtainable for many radiotherapy departments.

Accounting for tumor motion is especially important for targets that respond best to escalated doses and hypo-fractionated treatment, due to the risk of depositing a large percentage of the prescription dose to surrounding healthy tissue. One such disease type is pancreatic cancer, which is in close proximity to multiple organs at risk (OARs), and treatment tolerability is often a limiting factor to deliverable dose to the target. In this case, MR-guided radiotherapy (MRgRT) has become one of the most desirable treatment modalities due to imaging with excellent soft tissue contrast and real-time tumor tracking. Recent studies have shown that MRgRT can provide excellent local control of disease with low rates of normal tissue toxicity.

However, the cost of establishing and maintaining an MRgRT program is extremely expensive and is not feasible for the majority of radiation oncology departments. Understanding patient specific respiratory motion using imaging methods such as cine MRI could help improve motion management and treatment delivery methods and reduce the necessity for excessively expensive treatment machines if the benefits of MR-Linac units could be translated to traditional x-ray guided radiotherapy.

MRgRT with real time tumor tracking can provide a valuable data source for accomplishing this task. During the duration of treatment delivery patients undergo 2D sagittal cine MRI with active tumor tracking for beam gating. Our institution has collected a unique dataset of multi-fraction cine MRI for 45 pancreatic cancer patients, which includes the abdomen and diaphragm within the field of view (FOV), as well as tumor tracking contours.

In this embodiment, pancreatic tumor and surrogate motion was analyzed for 45 patients with 5 treatment fractions each, for a total of 225 treatment fractions, then applied multiple tumor position prediction models to assess the accuracy of intra-fraction position predictions based on x-ray visible surrogates.

Methods

This embodiment includes 45 retrospectively selected pancreatic cancer patients treated at our institution, from an original cohort of 50. Five patients were excluded due to incomplete image coverage of the abdomen or diaphragm. All patients underwent five fractions of MRgRT on a 0.35 T ViewRay MRIdian MR-Linac system (ViewRay, Oakwood Village, Ohio). Treatment fractions included real time tumor tracking using sagittal 2D cine MRI acquired at 4 frames per second (FPS). The sagittal 2D cine imaging parameters were TR/TR=2.1/0.91 ms, flip angle=60°, rBH=1351 Hz/pixel, FOV=350×350×7 mm3, and imaging patrix=100×100×1. All clinical images were then automatically interpolated by the ViewRay treatment delivery system (TDS) to a matrix size of 466×466×1 pixels, with a pixel size of 0.75×0.75 mm2. The first 1000 imaging frames from each cine MRI acquisition were used, for a total of 214,559 images from 225 fractions. The first 1000 imaging frames were used due to the time required to create and examine contours on each frame. For the five fractions displaying the 1st, 25th, 50th, 75th, and 100th percentile superior-inferior (SI) tumor motion range, all frames were used, ranging from 2981 to 6331 frames per fraction with the initial 700 frames used for training.

2.1 Region Delineation and Motion Quantification

The treatment target was delineated automatically by the ViewRay system in real time as images were acquired during treatment, which included a small area of soft tissue surrounding the tumor. After treatment was completed, cine MRI images with embedded contours were exported from the treatment system. An in-house software titled MAXgRT, developed in MATLAB 2020B (Mathworks, Natick, MA), was then used to extract contours and semi-automatic contouring of the diaphragm and the anterior abdominal surface.

Due to the additional tissue included in the clinical contour, an in-house tumor contour was generated by automatically deforming the clinical contour to reduce surrounding tissue and generate a tighter in-house tumor contour. This was done so that the center of mass calculation for the target position was more accurate. The active contouring, or snakes, method was used to delineate the tumor region based on the original contour. This method was based on the Chan-Vese model, which is able to implement segmentation of objects without clearly defined boundaries in images that would not be suitable to segmentation by thresholding or gradient based methods. The Chan-Vese model attempts to iteratively minimize an energy function with weighted values corresponding to the sum of intensity differences from the average values inside and outside the contour region, and a term dependent on the length of the contour boundary. The clinical tumor contour from the ViewRay system and the in-house tumor contour were used to generate two center of mass coordinates on each cine MRI frame, which served as the tumor position coordinate.

After automatic generation of the in-house contour MAXgRT provided semi-automatic contouring of the diaphragm and the anterior abdominal surface. For diaphragm contouring, the MAXgRT software requires an initial user designated contour. The snakes algorithm is applied to the user contour on the initial frame, and each subsequent frame uses the prior frame's contour as the starting point for the snakes algorithm. After the contours were generated, any mismatches were manually corrected slice-by-slice. Each column containing the diaphragm contour served as a sample for the SI motion direction.

The abdominal surface contour was generated by MAXgRT from a user defined boundary region. The boundary region was set to extend 12 cm inferiorly from the base of the rib cage, which encompassed the region of greatest motion. The snakes algorithm was again used to detect the boundary between abdominal surface and the image background. Similar to the diaphragm contour, each row of the abdominal surface contour was used as a sample for the anterior-posterior (AP) motion direction. The abdominal contour creation window and example contours are shown in FIGS. 15A-C. Prior to providing contour information to the motion models, all contours were manually checked and corrected if needed.

FIGS. 15A-C depict example images from the MAXgRT software of the abdominal contour window (window), generated contour for the first frame (first frame), and the generated contour for a random slice (later frame). Each row indicates a different patient from this study. The green line indicates the abdominal contour and the cyan line indicates the diaphragm contour.

2.2 Tumor Position Prediction Models

Tumor position prediction was performed using contour information from 1) only the abdomen AP position, 2) only the diaphragm SI position, and 3) the combination of abdomen SI position with diaphragm AP position. Two modeling approaches were applied for each surrogate combination. Model 1 was a ridge regression model based on the relationship between tumor center and the surrogates from the same frame. The linear models for X (AP) and Y (SI) position prediction and objective functions with L-2 norm regularization are described by equation 1.

$$X_{t,p} = a + \sum_{i=1}^{n} w_{d,i} X_{d,i} + \sum_{i=1}^{n} w_{a,l} Y_{a,l} \text{ with } \sum_{1}^{N}\left(X_t - \left(a + \sum_{i=1}^{n} w_{d,i} X_{d,i} + \sum_{i=1}^{n} w_{a,l} Y_{a,l}\right)\right)^2 + \left\|\sum_{i=1}^{n} w_{d,i} + \sum_{i=1}^{n} w_{a,l}\right\| < \varepsilon$$

$$Y_{t,p} = a + \sum_{i=1}^{n} w_{d,i} X_{d,i} + \sum_{i=1}^{n} w_{a,l} Y_{a,l} \text{ with } \sum_{1}^{N}\left(Y_t - \left(a + \sum_{i=1}^{n} w_{d,i} X_{d,i} + \sum_{i=1}^{n} w_{a,l} Y_{a,l}\right)\right)^2 + \left\|\sum_{i=1}^{n} w_{d,i} + \sum_{i=1}^{n} w_{a,l}\right\| < \varepsilon$$

(1)

Where N is the number of images, n is the number of image pixels along the X or Y dimension, $X_t$ and $Y_t$ are the true X and Y position of the tumor center, $X_{(t,p)}$ and $Y_{(t,p)}$ are the predicted AP and SI position of the tumor center, $X_{(d,i)}$ is the X position on the Y projection at the i-th pixel from the abdomen contour, $Y_{(a,l)}$ is the Y position on the X projection at the l-th pixel from diaphragm contour, $w_{(d,i)}$ and $w_{(a,l)}$ are weighting factors for each pixel, and c=0.01. For diaphragm only modeling all abdomen coefficients were set to 0 and for abdomen only modeling all diaphragm coefficients were set to 0.

Model 2 utilized principal component analysis (PCA) to optimize the dimensions of each feature. The linear models on principle component space for AP and SI position prediction and objective functions with L-2 norm regularization are described by equation 2.

$$P_x(P_{x,1}, P_{x,2}, \ldots, P_{x,R}) = PCA\begin{pmatrix} X_{t,1} & X_{d11}, Y_{a11} & \cdots & X_{d1,n}, Y_{a1,n} \\ \vdots & \vdots & \ddots & \vdots \\ X_{t,N} & X_{dN1}, Y_{aN1} & \cdots & X_{dN,n}, Y_{aN,n} \end{pmatrix}$$

$$X_{t,p} = a + \sum_{i=1}^{R} w_i P_{x,i} \text{ with } \sum_{1}^{N}\left(X_t - \left(a + \sum_{i=1}^{R_{95}} w_i P_{x,i}\right)\right)^2 + \left\|\sum_{i=1}^{R_{95}} w_i\right\| < \varepsilon$$

$$P_y(P_{y,1}, P_{y,2}, \ldots, P_{y,R}) = PCA\begin{pmatrix} Y_{t,1} & X_{d11}, Y_{a11} & \cdots & X_{d1,n}, Y_{a1,n} \\ \vdots & \vdots & \ddots & \vdots \\ Y_{t,N} & X_{dN1}, Y_{aN1} & \cdots & X_{dN,n}, Y_{aN,n} \end{pmatrix} Y_{t,p}$$

$$= a + \sum_{i=1}^{R} w_i P_{y,i} \text{ with } \sum_{1}^{N}\left(Y_t - \left(a + \sum_{i=1}^{R_{95}} w_i P_{y,i}\right)\right)^2 + \left\|\sum_{i=1}^{R_{95}} w_i\right\| < \varepsilon$$

(2)

Where P_x and P_y are the principal components from principal component analysis, R_95 are the components taken with a cumulative explained variance over 95%, N is the number of images, n is the number of image pixels along the X or Y dimension, and c=0.01. The intra-fraction models were trained using 70% of the frames from each fraction and tested with the remaining 30% of frames from the coinciding fraction.

The model predictions were then evaluated using mean squared error regression loss (MSE) described by equation 3 and mean absolute error regression loss (MAE) described by equation 4.

$$MSE = \frac{1}{N \text{ samples}} \sum^{N \text{ samples}} (\text{Prediction} - \text{Truth})^2 [\text{mm}^2] \quad (3)$$

$$MAE = \frac{1}{N \text{ samples}} \sum^{N \text{ samples}} |\text{Prediction} - \text{Truth}| [\text{mm}] \quad (4)$$

These metrics were applied to the anterior-posterior (AP) and superior-inferior (SI) directions separately.

Results 3.1 Motion Range 3.1.1 Tumor Motion

Tumor motion range was similar between the clinical contour and the in-house contour, as expected. The clinical contour had an average displacement of 7.3±2.6 mm in the AP direction, and 14.7±5.7 mm in the SI direction, while the in-house contour showed a displacement of 7.4±2.7 mm and 14.9±5.8 mm in the AP and SI directions, respectively. FIG. 14A shows the extent of tumor displacement in the AP and SI directions for both the clinical and in-house tumor contours.

FIG. 16A depicts the tumor contour displacement in the anterior-posterior (AP) and superior-inferior (SI) directions for the clinical and in-house tumor contours. FIG. 16B depicts the diaphragm and abdomen contour displacements in the AP and SI directions, respectively. For both plots, the bottom and top edge of the box indicate the 25th and 75th percentile, respectively, outlier data points are indicated with the + symbol.

Individual patients had a significant range in tumor motion, with a minimum motion of 2.8 mm to a maximum of 18.5 mm in the AP direction, and from 4.8 mm to maximum of 34.7 mm in the SI direction. FIG. 17 shows a heat map of the accumulated contour positions from each cine MRI frame for five patients, which represent the 1st, 25th, 50th, 75th, and 100th percentile motion range in the SI direction, as well as the paired SI motion trace over the first one hundred cine MRI frames. The gaps in the tumor motion trace indicate regions where cine MRI was not used for the treatment delivery system to generate a tumor contour, this generally occurs during gantry motion and not when beam gating is in progress.

FIG. 18 depicts intra-fraction variation of pancreatic tumor contour position normalized to the number of total acquired frames for five patients representing the $1^{st}$, $25^{th}$, $50^{th}$, $75^{th}$, and $100^{th}$ percentile motion range in the superior-inferior (SI) direction, as well as the paired anterior-posterior (AP) and SI motion trace over the first two hundred cine MRI frames. Regions of motion plots that are empty indicate that the treatment delivery system was unable to track the target at that point in time.

3.1.2 Surrogate Motion

The abdomen contour had a motion range of 2.8 mm to a maximum displacement of 25.9 mm and the diaphragm contour had a motion range of 3.8 mm to a maximum displacement of 49.7 mm. FIG. 16B shows the extent of diaphragm and abdomen motion, including outliers. FIG. 18 shows a comparison of surrogate and pancreatic tumor contour motion in the AP and SI directions for the same five patients shown above.

FIG. 18 depicts pancreatic tumor and surrogate contour motion in the anterior-posterior (AP) and superior-inferior (SI) directions for five patients representing the 1st, 25th, 50th, 75th, and 100th percentile tumor motion range in the SI direction. The red line represents the tumor position in both AP and SI graphs. The green line represents abdomen motion, and the blue line represents the diaphragm motion. The blue and green arrows indicate the position of the abdomen and diaphragm contours, respectively.

3.2 Intra-fraction Tumor Position Prediction Error 3.2.1 Tumor Position Prediction Error Using Abdomen Surrogate Table 1 displays the MSE and MAE of intra-fraction pancreatic tumor position prediction using only the abdomen contour surrogate. The 95th percentile MSE was 1.2 mm2 (mean: 0.5 mm2, max.: 4.4 mm2) and 4.3 mm2 (mean: 1.3 mm2, max.: 11.2 mm2) in the AP and SI directions for the ridge regression model, while the PCA model had a 95th percentile MSE of 1.1 mm2 (mean: 0.4 mm2, max.: 3.8 mm2) and 3.6 mm2 (mean: 1.3 mm2, max.: 12.3 mm2) in the AP and SI directions. The ridge regression model also had a 95th percentile MAE of 0.9 mm (mean: 0.5 mm, max.: 1.6 mm) and 1.5 mm (mean: 0.8 mm, max.: 2.6 mm) in the AP and SI directions, with the PCA model having values of 0.8 mm (mean: 0.5 mm, max.: 1.4 mm) and 1.4 mm (mean: 0.8 mm, max.: 2.7 mm).

TABLE 1

The mean (±1SD) and minimum to maximum range of mean squared error (MSE) and mean absolute error (MAE) for intra-fraction tumor position prediction models in the anterior-posterior (AP) and superior-inferior (SI) directions utilizing only the abdomen AP position.

| | AP | | | | SI | | | |
|---|---|---|---|---|---|---|---|---|
| | MSE (mm$^2$) | | MAE (mm) | | MSE (mm$^2$) | | MAE (mm) | |
| | Mean | Range | Mean | Range | Mean | Range | Mean | Range |
| Ridge - Clinical Contour | 0.4 ± 0.4 | 0.1-4.3 | 0.5 ± 0.2 | 0.2-1.6 | 1.2 ± 1.3 | 0.2-10.6 | 0.8 ± 0.3 | 0.4-2.6 |
| Ridge - In-house Contour | 0.5 ± 0.4 | 0.1-4.4 | 0.5 ± 0.2 | 0.2-1.6 | 1.3 ± 1.5 | 0.1-11.2 | 0.8 ± 0.4 | 0.3-2.6 |
| PCA - Clinical Contour | 0.4 ± 0.3 | 0.1-3.4 | 0.4 ± 0.2 | 0.2-1.4 | 1.3 ± 1.5 | 0.2-12.8 | 0.8 ± 0.3 | 0.4-2.9 |
| PCA - In-house Contour | 0.4 ± 0.4 | 0.1-3.8 | 0.5 ± 0.2 | 0.2-1.4 | 1.3 ± 1.5 | 0.2-12.3 | 0.8 ± 0.4 | 0.3-2.7 |

3.2.2 Tumor Position Prediction Error Using Diaphragm Surrogate

Table 2 displays the MSE and MAE of intra-fraction pancreatic tumor position prediction using only the diaphragm contour surrogate. The 95th percentile MSE was 1.0 mm2 (mean: 0.4 mm2, max.: 5.8 mm2) and 3.1 mm2 (mean: 1.1 mm2, max.: 17.5 mm2) in the AP and SI directions for the ridge regression model, while the PCA model had a 95th percentile MSE of 1.1 mm2 (mean: 0.4 mm2, max.: 3.7 mm2) and 3.7 mm2 (mean: 1.3 mm2, max.: 14.0 mm2) in the AP and SI directions. The ridge regression model also had a 95th percentile MAE of 0.8 mm (mean: 0.5 mm, max.: 1.4 mm) and 1.3 mm (mean: 0.7 mm, max.: 2.3 mm) in the AP and SI directions, with the PCA model having values of 0.8 mm (mean: 0.5 mm, max.: 1.4 mm) and 1.4 mm (mean: 0.8 mm, max.: 2.9 mm).

TABLE 2

The mean (±1SD) and minimum to maximum range of mean squared error (MSE) and mean absolute error (MAE) for intra-fraction tumor position prediction models in the anterior-posterior (AP) and superior-inferior (SI) directions utilizing only the diaphragm SI position.

|  | AP | | | | SI | | | |
|---|---|---|---|---|---|---|---|---|
|  | MSE (mm$^2$) | | MAE (mm) | | MSE (mm$^2$) | | MAE (mm) | |
|  | Mean | Range | Mean | Range | Mean | Range | Mean | Range |
| Ridge - Clinical Contour | 0.4 ± 0.5 | 0.1-5.0 | 0.4 ± 0.2 | 0.2-1.4 | 1.1 ± 1.7 | 0.2-20.7 | 0.7 ± 0.3 | 0.3-2.3 |
| Ridge - In-house Contour | 0.4 ± 0.5 | 0.1-5.8 | 0.5 ± 0.2 | 0.2-1.4 | 1.1 ± 1.6 | 0.2-17.5 | 0.7 ± 0.3 | 0.3-2.4 |
| PCA - Clinical Contour | 0.4 ± 0.4 | 0.1-3.7 | 0.5 ± 0.2 | 0.2-1.4 | 1.3 ± 1.5 | 0.2-12.8 | 0.8 ± 0.4 | 0.4-2.9 |
| PCA - In-house Contour | 0.4 ± 0.4 | 0.1-3.7 | 0.5 ± 0.2 | 0.2-1.4 | 1.3 ± 1.6 | 0.2-14.0 | 0.8 ± 0.4 | 0.3-2.9 |

3.2.3 Tumor Position Prediction Error Using Two Surrogates

The MSE and MAE of using both the abdomen and diaphragm contour surrogates to predict intra-fraction pancreatic tumor position are shown in table 3. Over all patients, the ridge regression model had a 95th percentile intra-fraction MSE of less than 1.5 mm2 (mean: 0.6 mm2, max.: 11.7 mm2) and 4.6 mm2 (mean: 1.8 mm2, max.: 76.78 mm2) in the AP and SI directions, respectively, and the 95th percentile MAE was less than 0.9 mm (mean: 0.6 mm, max.: 2.2 mm) and 1.8 mm (mean: 0.9 mm, max.: 1.8 mm), in the AP and SI directions, respectively. For the PCA model, 95th percentile intra-fraction MSE was less than 1.7 mm2 (mean: 0.6 mm2, max.: 5.6 mm2) and 4.9 mm2 (mean: 1.4 mm2, max.: 13.3 mm2) in the AP and SI directions, and the 95th percentile MAE was less than 1.0 mm (mean: 0.6 mm, max.: 2.1 mm) and 1.7 mm (mean: 0.8 mm, max.: 2.9 mm) in the AP and SI directions.

TABLE 3

The mean (±1SD) and minimum to maximum range of mean squared error (MSE) and mean absolute error (MAE) for intra-fraction tumor position prediction models in the anterior-posterior (AP) and superior-inferior (SI) directions.

|  | AP | | | | SI | | | |
|---|---|---|---|---|---|---|---|---|
|  | MSE (mm$^2$) | | MAE (mm) | | MSE (mm$^2$) | | MAE (mm) | |
|  | Mean | Range | Mean | Range | Mean | Range | Mean | Range |
| Ridge - Clinical Contour | 0.5 ± 0.6 | 0.1-4.8 | 0.5 ± 0.2 | 0.2-1.5 | 1.8 ± 5.4 | 0.2-76.9 | 0.9 ± 0.4 | 0.4-3.4 |
| Ridge - In-house Contour | 0.6 ± 0.9 | 0.1-11.7 | 0.6 ± 0.3 | 0.2-2.2 | 1.8 ± 5.4 | 0.1-76.8 | 0.9 ± 0.5 | 0.3-3.4 |
| PCA - Clinical Contour | 0.6 ± 0.6 | 0.1-4.4 | 0.6 ± 0.3 | 0.2-2.0 | 1.3 ± 1.5 | 0.2-11.7 | 0.8 ± 0.4 | 0.4-2.7 |
| PCA - In-house Contour | 0.6 ± 0.7 | 0.1-5.6 | 0.6 ± 0.3 | 0.2-2.1 | 1.4 ± 1.7 | 0.2-13.3 | 0.8 ± 0.4 | 0.3-2.9 |

3.2.4 Full Fraction Tumor Position Prediction Error

For the five patients displayed above, which demonstrated the 1st, 25th, 50th, 75th, and 100th percentile tumor motion range in the SI direction, motion models were generated using 700 training frames and applied to all acquired frames. The MSE in the AP and SI motion directions for models based on the abdominal, diaphragm, or combined contour positions are shown in table 4.

TABLE 4

The mean squared error (MSE) for intra-fraction tumor position prediction models using 700 training images and applied to the entirety of the remaining frames in the anterior-posterior (AP) and superior-inferior (SI) directions, with the clinical tumor contour.

|  |  | MSE AP (mm) | | MSE SI (mm) | |
| --- | --- | --- | --- | --- | --- |
|  |  | Ridge | PCA | Ridge | PCA |
| $1^{st}$ | Abd | 0.5 | 0.5 | 5.6 | 5.7 |
| percentile | Dia | 4.8 | 0.5 | 2.3 | 5.7 |
|  | Abd + Dia | 3.0 | 4.8 | 0.8 | 1.8 |
| $25^{th}$ | Abd | 1.3 | 1.3 | 4.2 | 4.2 |
| percentile | Dia | 0.5 | 1.3 | 1.8 | 4.2 |
|  | Abd + Dia | 1.1 | 1.1 | 4.5 | 4.7 |
| $50^{th}$ | Abd | 2.2 | 2.2 | 3.5 | 3.6 |
| percentile | Dia | 3.0 | 2.2 | 5.5 | 3.6 |
|  | Abd + Dia | 5.6 | 6.1 | 3.9 | 4.6 |
| $75^{th}$ | Abd | 0.5 | 0.5 | 1.6 | 1.6 |
| percentile | Dia | 0.7 | 0.8 | 0.9 | 1.0 |
|  | Abd + Dia | 0.5 | 0.5 | 0.8 | 1.0 |
| $100^{th}$ | Abd | 1.9 | 1.9 | 7.6 | 7.6 |
| percentile | Dia | 4.5 | 1.9 | 4.0 | 7.6 |
|  | Abd + Dia | 2.3 | 2.4 | 2.9 | 3.1 |

Abd: abdominal contour-based model;
Dia: diaphragm contour-based model;
Abd + Dia: abdominal and diaphragm contour-based model

Discussion

Real-time tumor tracking during MRgRT for pancreatic cancer provides a valuable tool for accurately delivering treatment where MR-Linac systems are available. However, due to the high cost of MR-Linac systems, the required infrastructure, and the clinical team required to support such systems, they are not easily accessible to the majority of radiation oncology clinics. This work utilized a unique dataset obtained from our institutional MR-Linac and treatment database to generate patient specific intra-fraction tumor position prediction models, using motion information from surrogates that are visible on x-ray imaging. Motion analysis of the 225 treatment fractions showed a large variation in the extent of motion present in the tumor, diaphragm, and abdominal contours. The largest tumor contour displacement was 18.5 mm in the AP direction, and 34.7 mm in the SI direction, much larger than standard treatment margin expansions, emphasizing the need for image guidance and real time target tracking to deliver safe and effective treatments. The pancreatic tumor motion range was similar to previously reported values. Knybel et al. reported a mean tumor motion of 11 mm in the SI direction tracked with the Synchrony respiratory tracking system (Accuracy Inc., Sunnyvale, CA), and Dolde et al. found a motion range of 3.7 mm to 28.5 mm using 4D MRI scans.

The motion models developed from the cine MRI images had an average intra-fraction MSE was 0.6 mm and 1.4 in the AP and SI directions, respectively, for the PCA model using both the abdomen and diaphragm surrogate information, less than the typical margin expansion of 5 mm used for pancreas tumors. This indicates the possibility for using surrogate-based tumor tracking without implanted fiducials. However, the accuracy of these models is most limited by the single 2D imaging plane and would benefit greatly from orthogonal imaging planes to provide information on the left-right (LR) tumor motion. Due to the nature of respiratory motion, the extent of pancreatic tumor motion in the LR plane is limited and is not currently tracked during treatment delivery. The motion range in the AP and SI directions for the diaphragm and pancreas were consistent with previous literature, indicating that the single 2D imaging plane did not significantly impact motion amplitude measurements.

Analysis of the tumor position prediction models showed that the abdomen surrogate only model provided the smallest average MSE and MAE values in the AP direction and the diaphragm surrogate only models provided the smallest average MSE and MAE values in the SI direction. In contrast, the models utilizing both surrogates to train the motion models resulted in the largest average MSE and MAE values in both the AP and SI directions. However, the difference between single and multiple surrogate model prediction error average values is well within the standard deviations for all cases. When the entire fraction was applied with 700 training images, the MSE increased, relative to the first 1000 frames. This was especially apparent for the SI direction. The average MSE for five fractions increased from 0.7 mm to 3.0 mm in the AP direction and from 1.0 mm to 3.0 mm in the SI direction for the full fraction PCA model. This may be due to changes in the respiratory pattern over the full fraction length, which ranged from 12.4 to 26.4 minutes in length with 2.9 minutes of training.

Future works will include the addition of inter-fraction models. Inter-fraction models are expected to have worse prediction error and require more complex model definitions due to the variation in respiratory motion that occurs over time, especially from day-to-day.[20, 21] To account for inter-fraction variation some baselining method is expected to provide a starting point for the prediction. Further model development is needed to account for such variation, and our future work looks to expand the model complexity and implement machine learning techniques. Another solution to inter-fraction variation would be the implementation of visual guidance for respiration, such as the system developed by Lewis et al. to limit the extent of motion and create a more repeatable setup.

Conclusion

This study evaluated pancreatic tumor motion and developed patient specific pancreatic tumor position prediction models for intra-fraction motion. The dataset of 225 treatment fractions across 45 patients with sagittal 2D cine MRI provided good quality images containing multiple surrogates to inform the motion models, and resulted in mean standard and absolute errors smaller than the usual target margin expansion. Small errors were found when one surrogate was used to predict tumor position, indicating it could be a useful tool with surface or fluoroscopic imaging. To the authors' knowledge, this is the first motion study of its kind, utilizing a large clinical dataset of MRgRT treatment data for assessing tumor and x-ray viable surrogate motion. Additionally, this approach could be extended to other abdominothoracic cancer sites, as well as utilize additional surrogates. We believe this is an important tool for the eventual improvement of pancreatic cancer treatment accuracy and tumor tracking abilities.

Example 6: Institutional Solution of Clinical Cine MRI for Tumor Motion Evaluation in Radiotherapy Purpose Since 4D-MRI is inadequate to capture dynamic respiratory variations, real-time cinematographic (cine) MRI is actively used in MR-guided radiotherapy (MRgRT) for tumor motion evaluation, delineation, and tracking. However, most radiotherapy imaging platforms do not support the format of cine MRI from clinical MRI systems. This study developed an institutional solution of clinical cine MRI for tumor motion evaluation in radiotherapy applications.

Methods

Cine MRI manipulation software (called Cine Viewer) was developed within a commercial Treatment Planning System (TPS). It consists of 1) single/orthogonal viewers, 2) display controllers, 3) measurement grids/markers, and 4) manual contouring tools.

Results

The institutional solution of clinical cine MRI incorporated with radiotherapy application was assessed through case presentations (liver cancer). Cine Viewer loaded cine MRIs from 1.5 T Philips Ingenia MRI, handling MRI DICOM format. The measurement grids and markers were used to quantify the displacement of anatomical structures in addition to the tumor. The contouring tool was utilized to localize the tumor and surrogates on the designated frame. The stacks of the contours were exhibited to present the ranges of tumor and surrogate motions. For example, the stacks of the tumor contours from case-1 were used to determine the ranges of tumor motions (~8.17 mm on the x-direction (AP-direction) and ~14 mm on the y-direction (SI-direction)). In addition, the patterns of the displacement of the contours over frames were analyzed and reported using in-house software. In the case-1 review, the tumor was displaced from +146.0 mm on the x-direction and +125.0 mm on the y-direction from the ROI of the abdominal surface.

Conclusion

The institutional solution of clinical cine MRI in radiotherapy was demonstrated. The proposed tools can streamline the utilization of cine MRI for tumor motion evaluation using Eclipse for treatment planning.

Introduction

Magnetic resonance imaging (MRI) is a highly desirable imaging modality compared to CT in radiotherapy because of MRI's superior soft-tissue contrast without ionizing radiation. 1 4D-MRI (respiratory-correlated or time-resolved) was introduced to the radiotherapy workflow in the place of 4D-CT to characterize the motion of mobile tumors and organs in the abdominothoracic regions.

To continuously irradiate the mobile tumor, the range of tumor motion, including a cycle-to-cycle variation of the breathing motion, must be included in radiotherapy target volumes. Since 4D-MRI is not adequate to capture dynamic respiratory variations, real-time cinematographic (cine) MRI is actively used in MR-guided radiotherapy (MRgRT) for tumor motion evaluation, delineation, and tracking. 5-9

Most radiotherapy imaging display platforms, however, do not support the file format of cine MRI from clinical MRI systems. Radiotherapy practice relies on MRI vendors' display tools, resulting in limited application of cine MRI. For example, currently, Velocity™ cancer imaging software and Eclipse™ Treatment Planning software (Varian Medical Systems Inc., CA, US) do not natively handle the format of cine MRI from clinical MRI simulators. In addition, the cine MRI of MRIdian system (ViewRay Inc., Ohio, US) is not currently compatible with other radiotherapy applications.

The study developed an institutional solution of clinical cine MRI for radiotherapy applications. The institutional solution included (1) tumor motion evaluation and (2) tumor contouring on cine MRI in a commercial treatment planning system. In addition, we developed supplementary in-house software to assess (3) tumor motion correlation with surrogates.

Methods

Cine MRI to Eclipse

For MRgRT, clinical cine MRIs were routinely acquired from a 1.5 T Ingenia MRI (Philips Healthcare, Amsterdam, Netherlands) in our institution. The anterior and posterior receiver array coils were in place for abdominothoracic MRI. Regular free-breathing 2D images in sagittal, coronal, and orthogonal planes (alternating sagittal-coronal planes) were acquired using the steady-state free precession MRI pulse sequence (Balanced Fast Field Echo: BFE) with an imaging field of view=350×350×7 mm3, voxel size=2.73× 2.73×7 mm3, and total acquisition time/frame≈250 ms. The acquisition rates were 4 FPS (frame per second) for sagittal and coronal orientations and 3.7 FPS for the orthogonal orientation for real-time imaging. Sequence parameters are reported in Table 5 in detail.

TABLE 5

Cine MRI sequence parameters

| Parameters | 2D Sag Cine 4 FPS | 2D Cor Cine 4 FPS | 2D Sag+Cor Cine 3.7 FPS |
|---|---|---|---|
| FOV (mm) | 350 × 350 × 7 | 350 × 350 × 7 | 350 × 350 × 7 |
| #Slices | 1 | 1 | 1 |
| NSA | 1 | 1 | 1 |
| Acquisition pixel (mm) | 3.1 × 3.1 × 7 | 3.1 × 3.1 × 7 | 3 × 3 × 7 |
| Reconstruction pixel (mm) | 2.73 × 2.73 × 7 | 2.73 × 2.73 × 7 | 2.73 × 2.73 × 7 |
| SENSE factor | 1 | 1 | 1 |
| Foldover Dir | AP | LR | AP/LR |
| Sequence type | BTFE | BTFE | BTFE |
| Flip Angle | 50° | 50° | 60° |
| Partial Fourier | 100% | 100% | 62.5% |
| rBW (Hz/pixel) | 1771.5 | 1771.5 | 1077.6 |
| Acquisition Time (s) | 0.25/frame | 0.25/frame | 0.135/image 0.225-0.269/frame |
| TE (ms) | 1.1 | 1.1 | 1.12-1.15 |

TABLE 5-continued

| | Cine MRI sequence parameters | | |
|---|---|---|---|
| Parameters | 2D Sag Cine 4 FPS | 2D Cor Cine 4 FPS | 2D Sag+Cor Cine 3.7 FPS |
| TR (ms) | 2.2 | 2.2 | 2.3 |
| Acquisition Matrix | 112 × 113 × 1 | 112 × 113 × 1 | 116 × 69 × 1 |
| Repetition frames | 238 | 238 | 520 |

Cine MRI manipulation software (Cine Viewer) was developed in the Eclipse Treatment Planning System (Varian Medical Systems, Palo Alto, CA) using the Eclipse Scripting Application Programming Interface (ESAPI, Ver. 15.6, Varian). ESAPI retrieves MRI meta-data and image pixel information for Cine Viewer by connecting to the patient data model generated via the connection between the TPS database and proprietarily formatted image repository. The Cine Viewer consists of 1) single/orthogonal viewers, 2) display controllers, 3) measurement grids/markers, and 4) manual contouring tools. Two display modes included 1) single plane displays for sagittal or coronal cine MRI and 2) orthogonal plane displays for alternating cine MRIs. The display controller tools include functions for display speed, contrast, and color map to improve cine display.

II.2 Evaluating Tumor Motion on Cine MRI Using Cine Viewer

The measurement grids and markers were used to quantify the displacement of anatomical structures. The grid tool was used to estimate the displacement of the structure by adjusting the size of the grids depending on the scale of the displacement.

The measurement markers were used to quantify the displacement of the structure using an internal distance calculated by the pixel resolution of the cine MRI. The measurement markers consist of horizontal and vertical markers (rotational position is not allowed). The horizontal markers were used to determine the displacement of the anatomical structure on the y-direction of the display plane. In the same way, the vertical markers were used to determine the displacement on the x-direction of the display plane.

II.3 Contouring Tumor on Cine MRI Using Cine Viewer

To improve the evaluation of the tumor motion, the manual contouring tool was used to spot the tumor on the designated frame. In addition, contours of the tumor and surrogates (e.g., diaphragm and/or abdomen) on multiple frames were drawn and exported for further evaluation and analysis.

II.4 Analyzing Tumor Motion Correlation with Surrogates

In addition to Cine Viewer in Eclipse, in-house software was developed using MATLAB (Mathworks, MA, USA) to assess the tumor motion in detail. The contours of the tumor and the surrogates on multiple frames were used to quantify the motion range and evaluate the motion correlation between tumors and surrogates.

II.5 Clinical Feasibility Evaluation

Clinical feasibility test of Cine Viewer was performed using cine MRIs of five liver cancer pa-tients (mean age: 67 years, range: 53~89) under IRB approval (retrospective study). Each patient underwent three cine MRI acquisitions as a part of standard care for MRgRT. The total imaging duration for the three cine series was about 3 minutes (250 ms×238 frames for the sagittal plane, 250 ms×238 frames for the coronal plane, and 135 ms×520 frames for the orthogonal planes).

III. Results

The institutional solution of clinical cine MRI incorporated with a radiotherapy application was assessed through five case presentations (five liver cancer patients).

III.1 Cine MRI to Eclipse

Cine Viewer was launched using the script of Varian Eclipse Scripting Application Programming Interface (ESAPI) in Eclipse shown in FIG. 19(a). The matrix of the display panel was 600×600 for a field of view of 350×350 mm2. In FIG. 19(b), sagittal or coronal cine MRIs were loaded on the single display panel with the display controller. The dual display panel displayed alternating cine MRIs in FIG. 19(c). The display controller includes functions for image contrast adjustment (window/level), color map selection, and image playback mode to improve the cine MRI presentation. The playback mode plays back images to the Cine Viewer that appeared on the MR scanner (image display mode).

III.2 Evaluating Tumor Motion on Cine MRI Using Cine Viewer

In the feasibility study, one of the authors (physicist) contoured based on the clinical target contour drawn by the physician on the 3D MRI in Eclipse. To demonstrate the function of the Cine Viewer such as the stack of the contours, cine frames from about two respiratory cycles (50 frames) were contoured. The tumor motion range can be quantified using two measurement tools: The grid and marker shown in FIG. 20. The grid tool was used to qualitatively evaluate the displacement of the structure. The size of the grids can be adjusted from 1 cm to 3 cm (in 1 cm intervals) depending on the scale of the measurements. Since the position of the grid was not adjustable, the grid tool was suitable for the approximation of the motion range.

In contrast, the measurement markers were used to precisely quantify the displacement of the structure as an internal ruler. Initially, one horizontal and one vertical markers were provided. Depending on the measurement direction, an additional marker with a proper name was added using the controller shown in FIG. 20(a). The other marker was paired with the initial marker, and the distance in the measured direction was reported on the report panel shown in FIG. 20(b). For example, two horizontal markers were used to determine the distance of the two markers on the y-direction, and two vertical markers were used for the distance of the two markers on the x-direction of the display plane shown in FIG. 20(a).

Two horizontal markers and two vertical markers were placed on the grid lines. They were separated by two cells of 3 cm-grid along the x- and y-direction. The distances on the report panel were 60.08 mm on the y-direction from the horizontal markers and 60.08 mm on the x-direction from the vertical markers, respectively. Since the resolution of the display panel was 0.58 mm (350 mm/600), there was a known limitation in the precision of the measurement.

III.3 Contouring Tumor on Cine MRI Using Cine Viewer

The manual contouring tool was utilized to localize the tumor on the designated frame in FIG. 21(a). Through the playback of the cine images, the displacement of the tumor was visualized and quantified using the measuring tools shown in FIG. 21(b). In addition to the tumor, the surrogates such as the diaphragm and abdomen on multiple frames were contoured to assess the motion correlation with the tumor. The stacks of the contours are presented in FIG. 21(c). For example, the stacks of the tumor contours were used to determine the ranges of tumor motion (~8.17 mm on the x-direction (AP-direction) and ~14 mm on the y-direction (SI-direction) using contour excursion) in FIG. 21(c). The coordinates of the contours were exported from the Cine Viewer for further motion assessments and analyses. Five liver cancer cases are presented in FIG. 21.

III.4 Analyzing Tumor Motion Correlation with Surrogates

In addition to assessing the tumor motion in the Cine Viewer, the in-house software was utilized to further visually (qualitatively) examine the motion correlation between the tumor and the surrogate motion as shown in FIG. 22(a). The contour-overlap function exhibited the stack of the contours to present the ranges of the surrogate motions in agreement with FIG. 21(c). The surrogate motions were reviewed to determine a region of interest (ROI).

Once the ROIs of the surrogates were selected, a wave window visualized patterns of the contour displacement over the frame in FIG. 22(b-c). For example, the displacement of the tumor (the central position of the tumor contour) was presented over the frames (the x- and y-directions) while the displacement of the diaphragm was on the y-direction and the displacement of the abdomen was on the x-direction. The size of the ROI windows can be adjusted to reduce the signal fluctuation. In addition, the distances between the tumor contour and the ROIs of the surrogates were automatically calculated and presented on the display panel in FIG. 22(a). This information was used to localize the tumor position based on the surrogate position. For example, the tumor was displaced from +147.0 mm on the x-direction and +118.5 mm on the y-direction from the ROI of the abdominal surface. Using the graph tool, the tumor motion range utilizing the center of a contour was quantified as ~6.5 mm on the x-direction (AP-direction) and ~17 mm on the y-direction (SI-direction)).

IV Discussion

This study presented our institutional solution of clinical cine MRI in Eclipse for tumor motion evaluation. It can be a pertinent approach for utilizing clinical cine MRI in radiotherapy setup. In addition to static 3D volumetric MRI for tumor and/or structure delineation, real-time cine MRI can benefit motion management and margin determination in treatment planning.

Tumor motion can be evaluated using 4D imaging techniques such as 4D-CT and 4D-MRI.2-4 Respiratory-correlated 4D imaging techniques suffer from cycle-to-cycle variations of the breathing motion, resulting in image artifacts and insufficient motion information. In contrast, time-resolved 4D-MRI can be a favorable technique but not clinically applicable yet due to scan time limitations. Alternatively, 2D cine MRI techniques are actively utilized in radiotherapy since 2D cine MRI can be fast enough to capture dynamic respiratory motion. Therefore, real-time cine MRI has already been employed in MR-guided radiotherapy (MRgRT) for tumor delineation and tracking. However, most radiotherapy imaging display platforms do not support the format of cine MRI, and radiotherapy practice relies on MRI vendors' proprietary tools. For example, cine MRI of ViewRay MRIdian system is only compatible with the vendor's treatment planning system. Otherwise, custom software disconnected from radiotherapy application has been developed to handle the cine MRI dataset. This approach needs further improvement for the full utilization of clinical cine MRI.

Our institutional solution (Cine Viewer) of clinical cine MRI was developed in the radiotherapy application (Eclipse) using Varian Eclipse Scripting Application Programming Interface (ESAPI). This approach made the tool available to clinical staff, including physicians, physicists, and dosimetrists. Using the solution connects the clinical cine MRI related to the radiotherapy workflow. We demonstrated the primary function of the Cine Viewer, such as motion evaluation using the measuring tools and contouring capability. The performance of the Cine Viewer grid and ruler measuring tools was verified. In addition, the software was verified by measuring the motion phantom with a known motion wave (MRI4D QUASAR motion phantom: ModusQA, Ontario, Canada) as shown in FIG. 23 (20 mm displacement in 15 cycles per minute of the sinusoidal curve). The Cine Viewer measurements were 1 grid in 2 cm grids and 19.83 mm from two horizontal markers. The dynamic range of the tumor motion can be visualized and determined using the display function shown in FIG. 21(c), unlike one breathing cycle of respiratory-correlated 4D imaging. Although the contours on cine MRI cannot be directly transferred to the treatment planning workflow, the range of the dynamic motion can be considered in margin determination.

In addition, the in-house software to evaluate the motion correlation between the tumor and the surrogates is presented. In beam delivery, the motion correlation between the tumor and surrogate is imperative if used for tumor motion monitoring. Evaluating the motion correlation between the tumor and the surrogates using the ROI in the in-house software (shown in FIG. 22(b&c)) can help clinical staff such as physicists and radiotherapists to select the proper monitoring ROI during gated beam delivery. The distance between the tumor and the ROI of the surrogate can be used to validate the tumor position in terms of the surrogate position.

The proposed tool has a few limitations. First, the institutional tool only handles 2D tumor motion since 2D cine MRI does not include 3D tumor motion. Although each imaging plane includes the essential motion along the superior-inferior direction, irregular tumor motion can shift the tumor out of the plane, resulting in different size of the tumor on the imaging plane. In the study, the orthogonal cine MRIs were acquired with 3.7 FPS which can provide the pseudo-3D tumor motion information. Second, the 2D contours in the proposed tool cannot be transferred to the 3D treatment planning platform in Eclipse. The motion range can be manually applied in margin expansion such as internal margin (IM). Third, the inter-fractional variation of the tumor motion cannot be considered using the proposed tool. However, the stack of the tumor motion using the proposed tool can estimate dynamic variations of the tumor motions, while respiratory-correlated 4D imaging techniques present one cycle of the tumor motion. Fourth, the institutional tool needs further improvement. For example, since the software displays a contour with a contour name, stacking the contours makes a stack of the contour names (FIG. 21). In addition, it was not fully automated, such as tumor contouring, motion range measurement, and margin creation from the stacks of the contours. Further improvement and development are ongoing.

The primary function of the proposed tool was discussed through the clinical case presentations. The study demonstrated the clinical feasibility of the proposed tool in a commercial TPS for the tumor motion evaluation in radiotherapy for treatment planning. After further development, tumor motion will be evaluated using the Cine Viewer in our routine clinical workflow. Furthermore, evaluating the correlation between tumors and surrogates can help clinical staff to exploit surface imaging-based motion management.

Conclusion

The institutional solution of clinical cine MRI in radiotherapy is demonstrated. The proposed tools can streamline the utilization of cine MRI for tumor motion evaluation using a radiotherapy application for treatment planning.

Exemplary embodiments of systems and methods of increasing spatial resolution of MR images are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A treatment targeting system comprising:
   a computing device including a processor and a memory, the memory storing instructions that when executed by the processor cause the processor to:
   receive magnetic resonance (MR) images of a subject including a target region;
   generate at least one contour of at least one surrogate element apart from the target region in the MR images; and
   determine a location of the target region in each of the MR images based on a location of the at least one contour in the MR images.

2. The treatment targeting system of claim 1, further comprising an MR imaging (MRI) device coupled to the computing device to generate the MR images of the subject.

3. The treatment targeting system of claim 2, further comprising a radiotherapy delivery device coupled to the treatment targeting system, wherein the target region includes a tumor and the instructions further cause the processor to operate the radiotherapy delivery device to direct radiotherapy at the target region based on the determined location of the target region in each of the MR images.

4. The treatment targeting system of claim 1, wherein the instructions cause the processor to generate at least one contour of at least one surrogate element by generating a first contour of a first surrogate element and generating a second contour of a second surrogate element.

5. The treatment targeting system of claim 4, wherein the instructions cause the processor to determine the location of the target region in each of the MR images based on a location of the first contour and the second contour in the MR images.

6. The treatment targeting system of claim 4, wherein the first surrogate element comprises the subject's diaphragm, and the second surrogate element comprises an anterior abdominal surface of the subject.

7. The treatment targeting system of claim 1, wherein the at least one surrogate element comprises the subject's diaphragm.

8. The treatment targeting system of claim 1, wherein the at least one surrogate element comprises an anterior abdominal surface of the subject.

9. The treatment targeting system of claim 1, wherein the instructions cause the processor to determine the location of the target region in each of the MR images based on the location of the at least one contour in the MR images using a ridge regression model based on a relationship between a center of the target area and the at least one surrogate element.

10. The treatment targeting system of claim 1, wherein the instructions cause the processor to determine the location of the target region in each of the MR images based on the location of the at least one contour in the MR images using principal component analysis (PCA).

11. The treatment targeting system of claim 1, wherein the received MR images are a plurality of first MR images having a first spatial resolution, and the instructions further cause the processor to:
   generate a plurality of second MR images having a second spatial resolution based on the plurality of first MR images using a neural network model, the second spatial resolution higher than the first spatial resolution, the neural network model is trained with a plurality of downsampled images downsampled from a plurality of training images as inputs and the plurality of training images as outputs; and
   generate the at least one contour of the at least one surrogate element and determine the location of the target region using the second MR images.

12. The treatment targeting system of claim 11, wherein the plurality of first MR images are a plurality of cine MR images.

13. The computer implemented method of claim 1, wherein the received MR images are a plurality of first MR images having a first spatial resolution, and the method further comprises:
   generating a plurality of second MR images having a second spatial resolution based on the plurality of first MR images using a neural network model, the second spatial resolution higher than the first spatial resolution, the neural network model is trained with a plurality of downsampled images downsampled from a plurality of training images as inputs and the plurality of training images as outputs; and
   generating the at least one contour of the at least one surrogate element and determine the location of the target region using the second MR images.

14. A computer implemented method of treatment targeting comprising:
   receiving magnetic resonance (MR) images of a subject including a target region;

generating at least one contour of at least one surrogate element apart from the target region in the MR images; and determining a location of the target region in each of the MR images based on a location of the at least one contour in the MR images.

15. The computer implemented method of claim 14, further comprising generating the MR images of the subject using an MR imaging (MRI) device.

16. The computer implemented method of claim 15, wherein the target region includes a tumor and the method further comprises directing, using a radiotherapy device, radiotherapy at the target region based on the determined location of the target region in each of the MR images.

17. The computer implemented method of claim 14, wherein generating at least one contour of at least one surrogate element apart from the target region in the MR images comprises generating a first contour of a first surrogate element and generating a second contour of a second surrogate element.

18. The computer implemented method of claim 17, wherein determining the location of the target region in each of the MR images based on a location of the at least one contour in the MR images comprises determining the location of the target region in each of the MR images based on a location of the first contour and the second contour in the MR images.

19. The computer implemented method of claim 14, wherein determining the location of the target region in each of the MR images based on the location of the at least one contour in the MR images comprises determining the location of the target region in each of the MR images based on the location of the at least one contour in the MR images using a ridge regression model based on a relationship between a center of the target area and the at least one surrogate element.

20. The computer implemented method of claim 14, wherein determining the location of the target region in each of the MR images based on the location of the at least one contour in the MR images comprises determining the location of the target region in each of the MR images based on the location of the at least one contour in the MR images using principal component analysis (PCA).

* * * * *